(12) United States Patent
Hakoshima

(10) Patent No.: US 12,374,160 B2
(45) Date of Patent: Jul. 29, 2025

(54) LINE-OF-SIGHT DETECTION DEVICE, LINE-OF-SIGHT DETECTION METHOD, AND COMPUTER-READABLE STORAGE MEDIUM

(71) Applicant: JVCKENWOOD Corporation, Yokohama (JP)

(72) Inventor: Shuji Hakoshima, Yokohama (JP)

(73) Assignee: JVCKENWOOD Corporation, Yokohama (JP)

( * ) Notice: Subject to any disclaimer, the term of this patent is extended or adjusted under 35 U.S.C. 154(b) by 51 days.

(21) Appl. No.: 18/403,782

(22) Filed: Jan. 4, 2024

(65) Prior Publication Data

US 2024/0153309 A1 May 9, 2024

Related U.S. Application Data

(63) Continuation of application No. PCT/JP2022/025367, filed on Jun. 24, 2022.

(30) Foreign Application Priority Data

Jul. 29, 2021 (JP) ................................ 2021-124572
Jul. 29, 2021 (JP) ................................ 2021-124620

(51) Int. Cl.
*G06V 40/19* (2022.01)
*G06T 7/70* (2017.01)
*G06V 10/141* (2022.01)

(52) U.S. Cl.
CPC ............... *G06V 40/19* (2022.01); *G06T 7/70* (2017.01); *G06V 10/141* (2022.01);
(Continued)

(58) Field of Classification Search
CPC .................................................. G06V 40/19
(Continued)

(56) References Cited

U.S. PATENT DOCUMENTS

2016/0262614 A1* 9/2016 Ninomiya .............. A61B 3/113
2018/0074581 A1 3/2018 Melman et al.
(Continued)

FOREIGN PATENT DOCUMENTS

JP 4649319 3/2011
JP 2017-211891 11/2017
(Continued)

OTHER PUBLICATIONS

International Search Report and Written Opinion for International Application No. PCT/JP2022/025367 mailed on Sep. 6, 2022, 11 pages.

*Primary Examiner* — Amir Shahnami
(74) *Attorney, Agent, or Firm* — Amin, Turocy & Watson, LLP

(57) ABSTRACT

A line-of-sight detection device includes a display unit configured to display an image, light sources configured to emit detection light to apply the detection light to an eyeball of a subject, an imaging unit configured to capture an image of the eyeball to which the detection light is applied, a position detection unit configured to detect, from the captured image, a position of a pupil center of the eyeball to which the detection light is applied and a position of a corneal reflex center, a gaze point detection unit configured to calculate a position of a gaze point of the subject based on the positions of the pupil center and corneal reflex center, and a light source control unit configured to change the light source for emitting the detection light among the light sources based on a target distance between the pupil center and the corneal reflex center.

7 Claims, 16 Drawing Sheets

(52) U.S. Cl.
CPC ............... *G06T 2207/10012* (2013.01); *G06T 2207/10152* (2013.01); *G06T 2207/30201* (2013.01)

(58) Field of Classification Search
USPC .......................................................... 348/78
See application file for complete search history.

(56) References Cited

U.S. PATENT DOCUMENTS

| | | |
|---|---|---|
| 2019/0191994 A1 | 6/2019 | Yamamoto et al. |
| 2020/0019241 A1 | 1/2020 | Ninomiya |

FOREIGN PATENT DOCUMENTS

| | | |
|---|---|---|
| JP | 2018-512665 | 5/2018 |
| JP | 2019-25195 | 2/2019 |
| WO | 2017/217026 | 12/2017 |

\* cited by examiner

LINE-OF-SIGHT DETECTION DEVICE, LINE-OF-SIGHT DETECTION METHOD, AND COMPUTER-READABLE STORAGE MEDIUM

CROSS-REFERENCE TO RELATED APPLICATIONS

This application is a Continuation of PCT International Application No. PCT/JP2022/025367 filed on Jun. 24, 2022 which claims the benefit of priority from Japanese Patent Applications No. 2021-124572 and No. 2021-124620, both filed on Jul. 29, 2021, the entire contents of all of which are incorporated herein by reference.

BACKGROUND

The present disclosure relates to a line-of-sight detection device, a line-of-sight detection method, and a computer-readable storage medium.

A line-of-sight detection device that causes a light source to emit detection light and apply the detection light to an eyeball of a subject, acquires an image of the eyeball to which the detection light is applied, calculates a pupil center and a corneal curvature center based on an image of a pupil and a reflected image of the detection light in the acquired image, and detects a vector extending from the corneal curvature center to the pupil center as a line-of-sight direction of the subject is known (for example, see Japanese Patent No. 4649319).

In the line-of-sight detection device as described above, the reflected image of the detection light applied to the eyeball of the subject may be present at a boundary between a cornea and a sclera or may be present in the sclera. The cornea and the sclera have different curvature radii, and therefore, in this case, detection accuracy of the line of sight may be reduced.

SUMMARY OF THE INVENTION

A line-of-sight detection device according to an aspect of the present disclosure includes: a display unit that displays an image; a plurality of light sources configured to emit detection light to apply the detection light to at least one of eyeballs of a subject; an imaging unit configured to capture an image of the eyeball to which the detection light is applied; a position detection unit configured to detect, from the captured image, a position of a pupil center that indicates a center of a pupil of the eyeball to which the detection light is applied and a position of a corneal reflex center that indicates a center of a corneal reflex; a gaze point detection unit configured to calculate a position of a gaze point of the subject based on the position of the pupil center and the position of the corneal reflex center; and a light source control unit configured to change the light source for emitting the detection light among the plurality of light sources based on a target distance between the pupil center and the corneal reflex center.

A line-of-sight detection method according to another aspect of the present disclosure includes: displaying an image on a display unit; emitting detection light from a plurality of light sources to apply the detection light to at least one of eyeballs of a subject; capturing an image of the eyeball to which the detection light is applied; detecting, from the captured image, a position of a pupil center that indicates a center of a pupil of the eyeball to which the detection light is applied and a position of a corneal reflex center that indicates a center of a corneal reflex; calculating a position of a gaze point of the subject based on the position of the pupil center and the position of the corneal reflex center; and changing the light source for emitting the detection light among the plurality of light sources based on a target distance between the pupil center and the corneal reflex center.

A non-transitory computer-readable storage medium according to still another aspect of the present disclosure stores a program for detecting a line-of-sight. The program causes a computer to execute: displaying an image on a display unit; emitting detection light from a plurality of light sources to apply the detection light to at least one of eyeballs of a subject; capturing an image of the eyeball to which the detection light is applied; detecting, from the captured image, a position of a pupil center that indicates a center of a pupil of the eyeball to which the detection light is applied and a position of a corneal reflex center that indicates a center of a corneal reflex; calculating a position of a gaze point of the subject based on the position of the pupil center and the position of the corneal reflex center; and changing the light source for emitting the detection light among the plurality of light sources based on a target distance between the pupil center and the corneal reflex center.

DETAILED DESCRIPTION

Embodiments of a line-of-sight detection device, a line-of-sight detection method, and a line-of-sight detection program according to the present disclosure will be described below based on the drawings. The present invention is not limited by the embodiments below. In addition, components in the embodiments described below include one that can be easily thought of by a person skilled in the art and one that is practically identical.

In the description below, a three-dimensional global coordinate system is set and positional relationships among the components will be described. It is assumed that a direction parallel to a first axis of a predetermined plane serves as an X-axis direction, a direction parallel to a second axis that is perpendicular to the first axis in the predetermined plane serves as an Y-axis direction, and a direction parallel to a third axis that is perpendicular to both of the first axis and the second axis serves as a Z-axis direction. The predetermined plane includes an XY plane.

Line-of-Sight Detection Device

Figure 1:
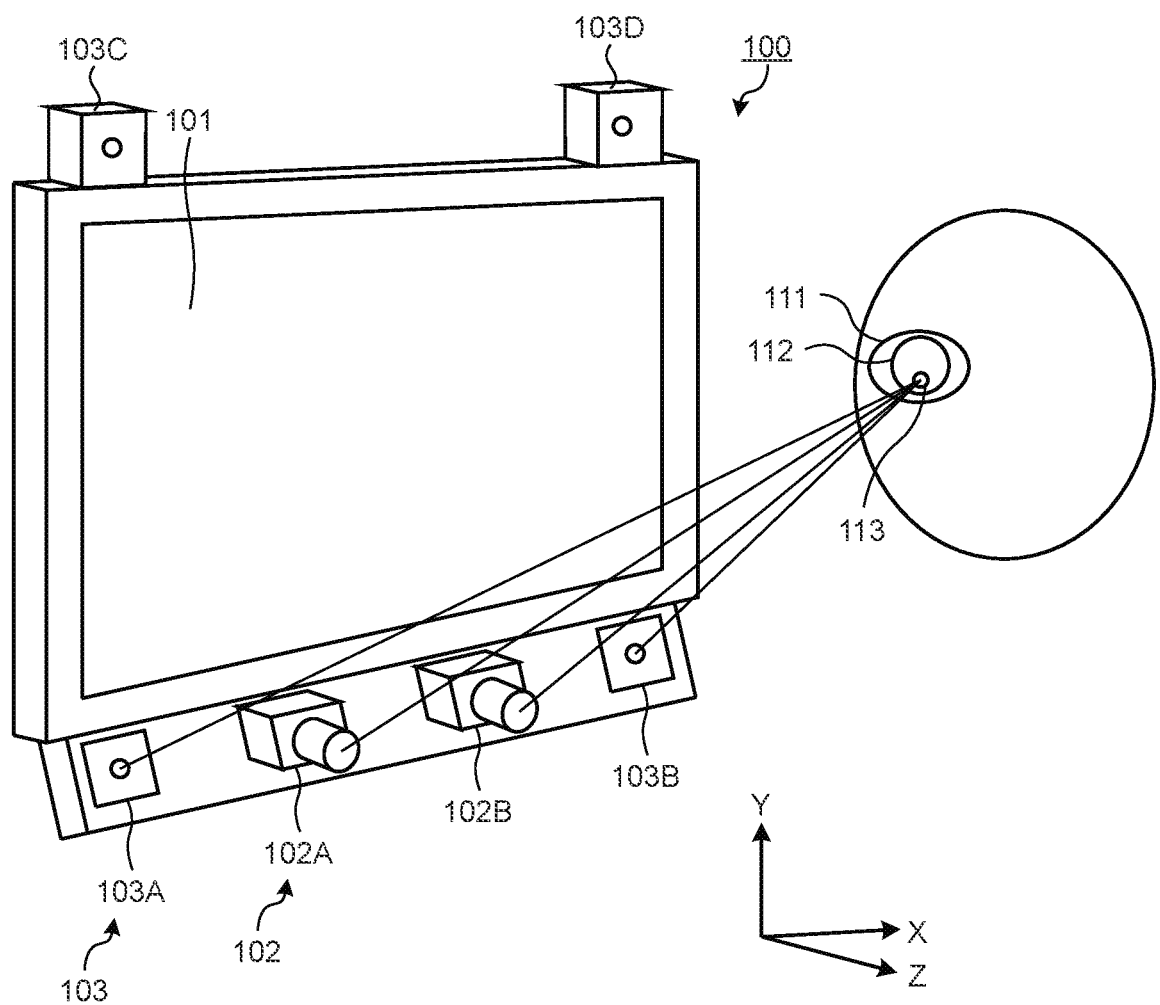
FIG. 1 is a perspective view schematically illustrating an example of a line-of-sight detection device according to the present embodiment.

FIG. 1 is a perspective view schematically illustrating an example of a line-of-sight detection device 100 according to the present embodiment. As illustrated in FIG. 1, the line-of-sight detection device 100 includes a display unit 101, a stereo camera device 102, and a lighting device 103.

The display unit 101 includes a flat panel display, such as a liquid crystal display (LCD) or an organic electroluminescence (EL) display (OELD). In the present embodiment, the display unit 101 displays an image. In the present embodiment, the display unit 101 displays an index for evaluating visual performance of a subject, for example. The display unit 101 is substantially parallel to the XY plane. The X-axis direction is a horizontal direction of the display unit 101, the Y-axis direction is a vertical direction of the display unit 101, and the Z-axis direction is a depth direction perpendicular to the display unit 101.

The stereo camera device 102 includes a first camera 102A and a second camera 102B. The stereo camera device 102 is arranged below the display unit 101. The first camera 102A and the second camera 102B are arranged in the X-axis direction. The first camera 102A is arranged in a negative X direction relative to the second camera 102B. Each of the first camera 102A and the second camera 102B includes an infrared camera, an optical system that is able to transmit near-infrared light with a wavelength of 850 nanometers (nm), and an imaging element that is able to receive the near-infrared light, for example.

The lighting device (light source) 103 includes a first light source (lower first light source) 103A, a second light source (lower second light source) 103B, a third light source (upper light source) 103C, and a fourth light source (upper light source) 103D. The first light source 103A and the second light source 103B are arranged below the display unit 101. The third light source 103C and the fourth light source 103D (upper light source) are arranged above the display unit 101. The first light source 103A and the second light source 103B are arranged in the X-axis direction. The first light source 103A is arranged in the negative X direction relative to the first camera 102A. The second light source 103B is arranged in a positive X direction relative to the second camera 102B. The third light source 103C and the fourth light source 103D are arranged in the X-axis direction. The third light source 103C is arranged in the negative X direction relative to the first camera 102A. The fourth light source 103D is arranged in the positive X direction relative to the second camera 102B.

Each of the first light source 103A, the second light source 103B, the third light source 103C and the fourth light source 103D includes a light emitting diode (LED) light source, and is able to emit near-infrared light with a wavelength of 850 nm, for example. Meanwhile, the first light source 103A and the second light source 103B may be arranged between the first camera 102A and the second camera 102B. Similarly, the third light source 103C and the fourth light source 103D may be arranged between the first camera 102A and the second camera 102B in the X direction. Further, the stereo camera device 102 may be arranged above the display unit 101.

The lighting device 103 emits near-infrared light as detection light and illuminates an eyeball 111 of the subject. The stereo camera device 102 captures an image of a part of the eyeball 111 (hereinafter, the "eyeball" also indicates a part of the eyeball) by the second camera 102B when the detection light that is emitted by light emission of the first light source 103A or the third light source 103C is applied to the eyeball 111, and captures an image of the eyeball 111 by the first camera 102A when the detection light that is emitted by light emission of the second light source 103B or the fourth light source 103D is applied to the eyeball 111.

At least one of the first camera 102A and the second camera 102B outputs a frame synchronous signal. The first light source 103A, the second light source 103B, the third light source 103C, and the fourth light source 103D emit the detection light based on the frame synchronous signal. The first camera 102A captures image data of the eyeball 111 when the detection light that is emitted from the second light source 103B or the fourth light source 103D is applied to the eyeball 111. The second camera 102B captures image data of the eyeball 111 when the detection light that is emitted from the first light source 103A or the third light source 103C is applied to the eyeball 111.

If the detection light is applied to the eyeball 111, a part of the detection light is reflected by a pupil 112, and light from the pupil 112 enters the stereo camera device 102. Further, if the detection light is applied to the eyeball 111, a corneal reflex image 113 that is a virtual image of a cornea is formed on the eyeball 111, and light from the corneal reflex image 113 enters the stereo camera device 102.

If relative positions between each of the first camera 102A and the second camera 102B and each of the first light source 103A, the second light source 103B, the third light source 103C, and the fourth light source 103D are appropriately set, intensity of light that is input from the pupil 112 to the stereo camera device 102 decreases and intensity of light that is input from the corneal reflex image 113 to the stereo camera device 102 increases. In other words, the image of the pupil 112 that is captured by the stereo camera device 102 has low luminance and the image of the corneal reflex image 113 has high luminance. The line-of-sight detection device 100 is able to detect a position of the pupil 112 and a position of the corneal reflex image 113 based on luminance of the captured image.

Figure 2:
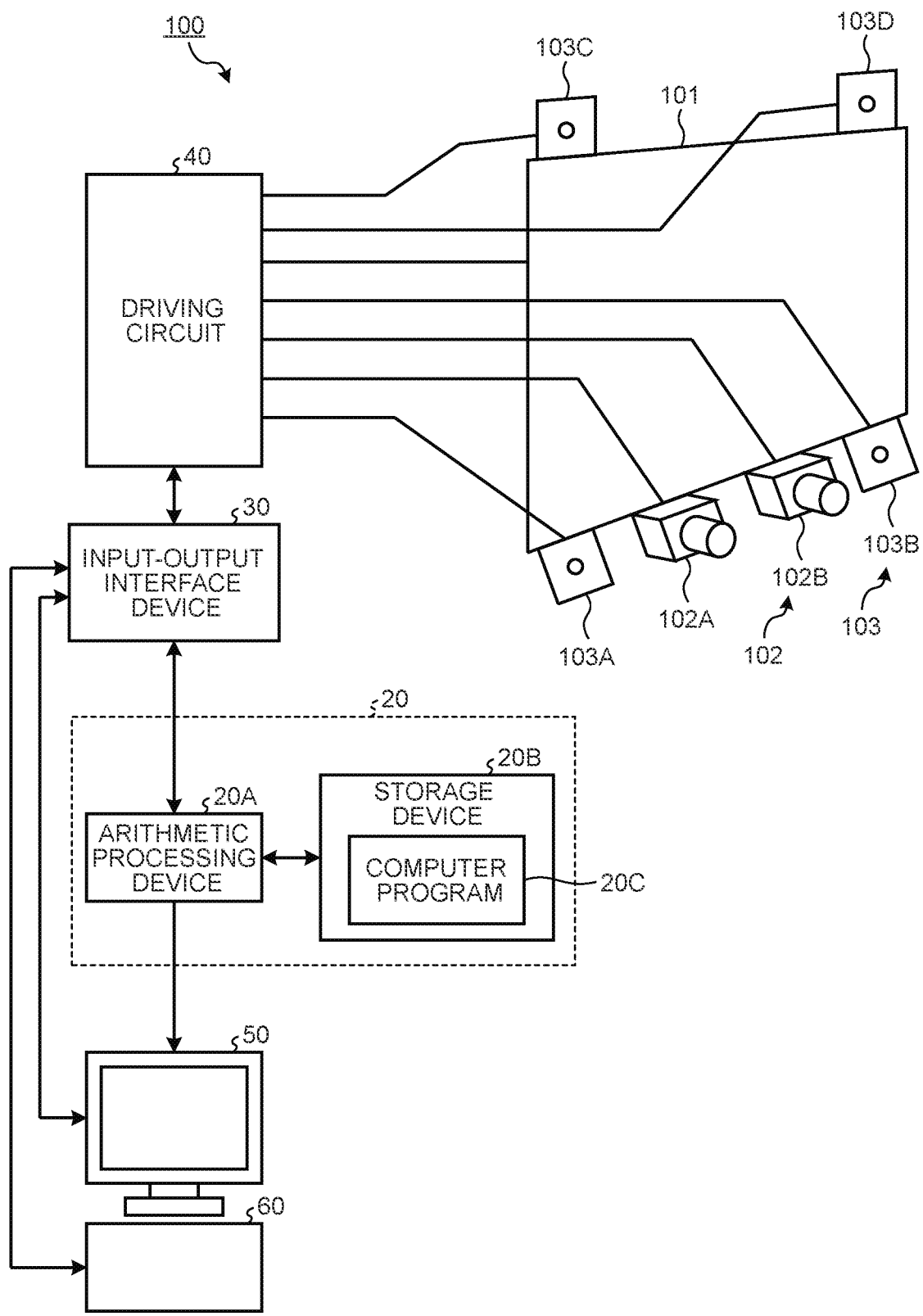
FIG. 2 is a diagram illustrating an example of a hardware configuration of the line-of-sight detection device according to the present embodiment.

FIG. 2 is a diagram illustrating an example of a hardware configuration of the line-of-sight detection device 100 according to the present embodiment. As illustrated in FIG. 2, the line-of-sight detection device 100 includes the display unit 101, the stereo camera device 102, the lighting device 103, a computer system (control unit) 20, an input-output interface device 30, a driving circuit 40, an output device 50, and an input device 60.

The computer system 20, the driving circuit 40, the output device 50, and the input device 60 perform data communication with one another via the input-output interface device 30. The computer system 20 includes an arithmetic processing device 20A and a storage device 20B. The arithmetic processing device 20A includes a microprocessor, such as a central processing unit (CPU). The storage device 20B includes a memory or a storage, such as a read only memory (ROM) and a random access memory (RAM). The arithmetic processing device 20A performs an arithmetic process in accordance with a computer program 20C that is stored in the storage device 20B.

The driving circuit 40 generates a driving signal and outputs the driving signal to the display unit 101, the stereo camera device 102, and the lighting device 103. Further, the driving circuit 40 supplies the image data of the eyeball 111 that is captured by the stereo camera device 102 to the computer system 20 via the input-output interface device 30.

The output device 50 includes a display unit, such as a flat panel display. Meanwhile, the output device 50 may include a printing device. The input device 60 generates input data by being operated. The input device 60 includes a keyboard or a mouse for the computer system. Meanwhile, it may be possible to include a touch sensor in which the input device 60 is arranged on a display screen of the output device 50 that is a display unit.

In the present embodiment, the display unit 101 and the computer system 20 are separate devices. Meanwhile, the display unit 101 and the computer system 20 may be integrated with each other. For example, if the line-of-sight detection device 100 includes a tablet personal computer, the computer system 20, the input-output interface device 30, the driving circuit 40, and the display unit 101 may be mounted on the tablet personal computer.

Figure 3:
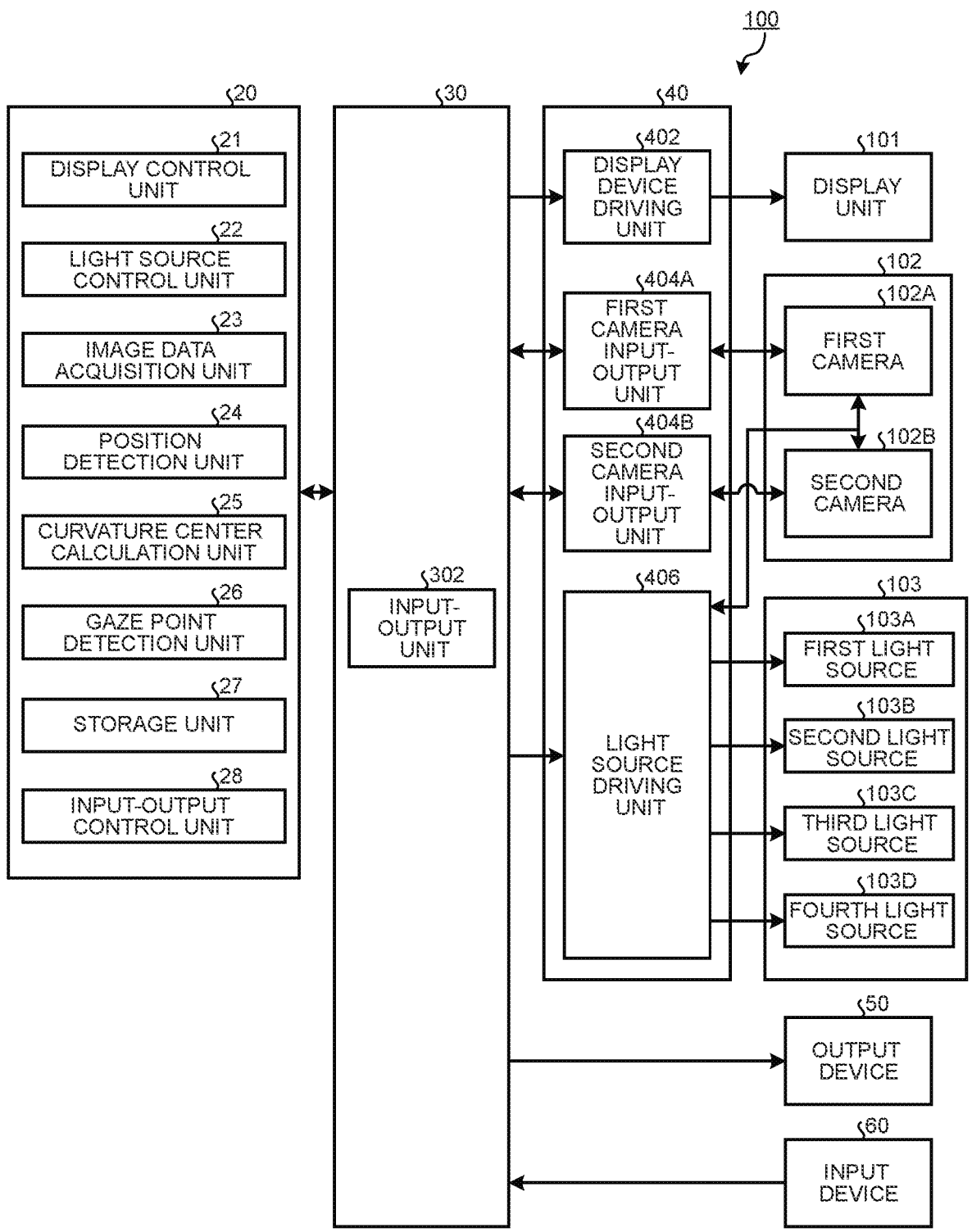
FIG. 3 is a functional block diagram illustrating an example of the line-of-sight detection device according to the present embodiment.

FIG. 3 is a functional block diagram illustrating an example of the line-of-sight detection device 100 according to the present embodiment. As illustrated in FIG. 3, the input-output interface device 30 includes an input-output unit 302. The driving circuit 40 includes a display device driving unit 402 that generates a driving signal for driving the display unit 101 and outputs the driving signal to the display unit 101, a first camera input-output unit 404A that generates a driving signal for driving the first camera 102A and outputs the driving signal to the first camera 102A, a second camera input-output unit 404B that generates a driving signal for driving the second camera 102B and outputs the driving signal to the second camera 102B, and a light source driving unit 406 that generates driving signals for driving the first light source 103A, the second light source 103B, the third light source 103C, and the fourth light source 103D and outputs the driving signals to the first light source 103A, the second light source 103B, the third light source 103C, and the fourth light source 103D. Further, the first camera input-output unit 404A supplies the image data of the eyeball 111 that is captured by the first camera 102A to the computer system 20 via the input-output unit 302. The second camera input-output unit 404B supplies the image data of the eyeball 111 that is captured by the second camera 102B to the computer system 20 via the input-output unit 302.

The computer system 20 controls the line-of-sight detection device 100. The computer system 20 includes a display control unit 21, a light source control unit 22, an image data acquisition unit 23, a position detection unit 24, a curvature center calculation unit 25, a gaze point detection unit 26, a storage unit 27, and an input-output control unit 28. Functions of the computer system 20 are implemented by the arithmetic processing device 20A and the storage device 20B.

The display control unit 21 displays an image to be viewed by the subject on the display unit 101. The display control unit 21 is able to display a target image in a calibration process at a plurality of positions (target positions) in the display unit 101, for example. The display control unit 21 may display the target image at each of target positions in a sequentially switching manner, or display the target image such that the target image moves to the plurality of target positions in sequence in the display unit 101. Meanwhile, the number of the target positions at which the target image is displayed may be set by input by an operator by using the input device 60 or the like, for example.

The light source control unit 22 controls the light source driving unit 406, and controls emission of light and non-emission of light from the first light source 103A, the second light source 103B, the third light source 103C, and the fourth light source 103D. The light source control unit 22 changes the light source for emitting the detection light among the first light source 103A, the second light source 103B, the third light source 103C, and the fourth light source 103D based on a target distance between the pupil center and a corneal reflex center. Examples of the target distance include a vertical distance between the pupil center and the corneal reflex center, a horizontal distance between the pupil center and the corneal reflex center, and a minimum distance between the pupil center and the corneal reflex center. If the target distance between the pupil center and the corneal reflex center is equal to or larger than a predetermined threshold while the first light source 103A and the second light source 103B emit the detection light, the light source control unit 22 is able to change the light sources such that the third light source 103C and the fourth light source 103D emit the detection light. Further, if the target distance between the pupil center and the corneal reflex center is equal to or larger than a predetermined threshold while the third light source 103C and the fourth light source 103D emit the detection light, the light source control unit 22 is able to change the light sources such that the first light source 103A and the second light source 103B emit the detection light.

Furthermore, the light source control unit 22 changes the light source for emitting the detection light among the first light source 103A, the second light source 103B, the third light source 103C, and the fourth light source 103D based on whether a shape of a reflected image of the detection light in the image of the eyeball 111 is included in a reference shape. In the present embodiment, the reference shape may be a single elliptical shape. When determining that the shape of the reflected image of the detection light in the image of the eyeball 111 is not included in the reference shape while the first light source 103A and the second light source 103B emit the detection light, the light source control unit 22 is able to change the light sources such that the third light source 103C and the fourth light source 103D emit the detection light. Moreover, when determining that the shape of the reflected image of the detection light in the image of the eyeball 111 is not included in the reference shape while the third light source 103C and the fourth light source 103D emit the detection light, the light source control unit 22 is able to change the light sources such that the first light source 103A and the second light source 103B emit the detection light.

The image data acquisition unit 23 acquires the image data of the eyeball 111 of the subject that is captured by the stereo camera device 102 that includes the first camera 102A and the second camera 102B, from the stereo camera device 102 via the input-output unit 302.

The position detection unit 24 detects positional data of the pupil center based on the image data of the eyeball 111 that is acquired by the image data acquisition unit 23. Further, the position detection unit 24 detects positional data of the corneal reflex center based on the image data of the eyeball 111 that is acquired by the image data acquisition unit 23. The pupil center is a center of the pupil 112. The corneal reflex center is a center of the corneal reflex image 113. The position detection unit 24 detects the positional data of the pupil center and the positional data of the corneal reflex center for each of the right eyeball 111 and the left eyeball 111 of the subject.

The curvature center calculation unit 25 calculates the positional data of a corneal curvature center of the eyeball 111 based on the image data of the eyeball 111 that is acquired by the image data acquisition unit 23.

The gaze point detection unit 26 detects positional data of a gaze point of the subject based on the image data of the eyeball 111 that is acquired by the image data acquisition unit 23. In the present embodiment, the positional data of the gaze point indicates positional data of an intersection point of a line-of-sight vector of the subject, which is defined by a three-dimensional global coordinate system, and the display unit 101. The gaze point detection unit 26 detects the line-of-sight vector of each of the right eyeball 111 and the left eyeball 111 of the subject based on the positional data of the pupil center and the positional data of the corneal curvature center that are acquired from the image data of the eyeball 111. After detection of the line-of-sight vector, the gaze point detection unit 26 detects the positional data of the gaze point that indicates the intersection point of the line-of-sight vector and the display unit 101.

The storage unit 27 stores therein various kinds of data and programs related to detection of the line of sight as described above. The storage unit 27 is able to store therein, for example, data about an image to be displayed on the display unit 101 for each color and each luminance of a background image. Further, the storage unit 27 stores therein the positional data of the gaze point that is calculated in each calibration process.

Furthermore, the storage unit 27 stores therein a line-of-sight detection program that causes a computer to perform a process of displaying an image on the display unit 101, a process of emitting the detection light from the plurality of light sources and applying the detection light to at least one of the eyeballs 111 of the subject, a process of capturing an image of the eyeball 111 to which the detection light is applied, a process of detecting, from the captured image, the position of the pupil center that indicates the center of the pupil of the eyeball 111 and the position of the corneal reflex center that indicates the center of the corneal reflex, a process of calculating the position of the gaze point of the subject based on the position of the pupil center and the position of the corneal curvature center, and a process of changing the light source for emitting the detection light among the plurality of light sources based on the target distance between the pupil center and the corneal reflex center.

Moreover, the storage unit 27 stores therein the line-of-sight detection program that causes a computer to perform a process of displaying an image on the display unit 101, a process of emitting the detection light from the plurality of light sources and applying the detection light to at least one of the eyeballs 111 of the subject, a process of capturing an image of the eyeball 111 to which the detection light is applied, a process of detecting, from the captured image, the position of the pupil center that indicates the center of the pupil of the eyeball 111 and the position of the corneal reflex center that indicates the center of the corneal reflex, a process of calculating the position of the gaze point of the subject based on the position of the pupil center and the position of the corneal curvature center, and a process of changing the light source for emitting the detection light among the plurality of light sources based on whether the shape of the corneal reflex image 113 of the detection light in the image of the eyeball 111 is included in the reference shape.

The input-output control unit 28 outputs data to at least one of the display unit 101 and the output device 50.

A process performed by the curvature center calculation unit 25 according to the present embodiment will be described below. In the present embodiment, a case will be described in which the first light source 103A and the second light source 103B illuminate the eyeball 111 and the two cameras, that is, the first camera 102A and the second camera 102B, capture images of the eyeball 111. Meanwhile, the same explanation will be applicable to not only the case in which the two light sources and the two cameras are used, but also a case in which a single light source and a single camera are used. A principle of the line-of-sight detection method according to the present embodiment will be described below.

Figure 4:
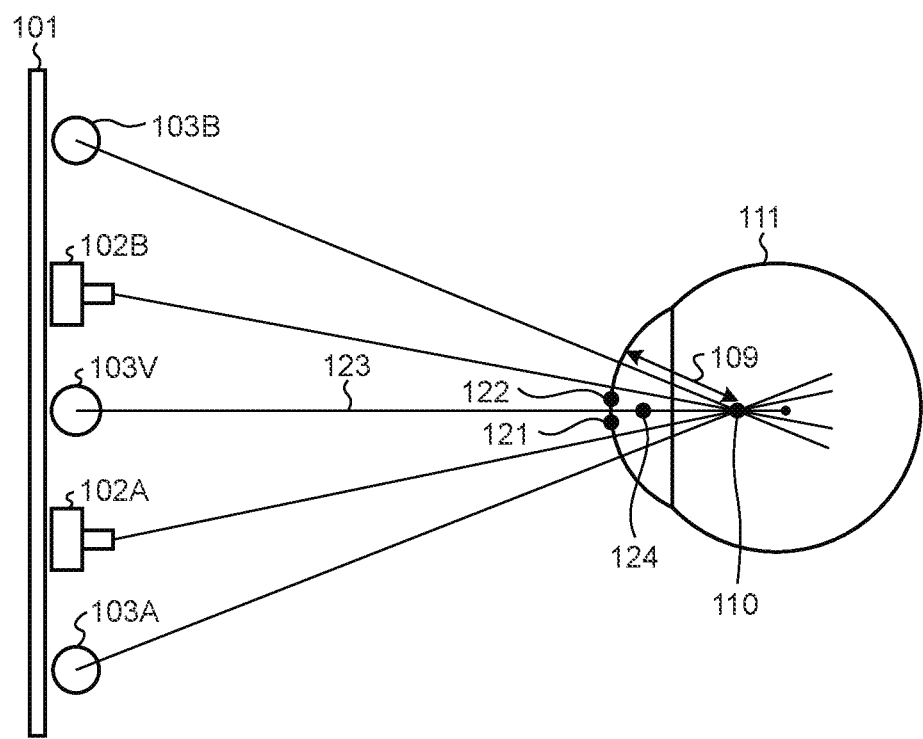
FIG. 4 is a diagram illustrating an example in which a first light source and a second light source illuminate an eyeball.
Figure 4:
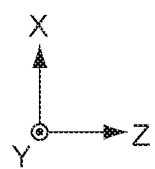

FIG. 4 is a diagram illustrating an example in which the first light source 103A and the second light source 103B illuminate the eyeball 111. As illustrated in FIG. 4, in the present embodiment, the first camera 102A and the second light source 103B are arranged so as to be symmetric to the second camera 102B and the first light source 103A with respect to a straight line that passes through an intermediate position between the first camera 102A and the second camera 102B. It is assumed that a virtual light source (a reference position of the light source) 103V is present at the intermediate position between the first camera 102A and the second camera 102B.

A corneal reflex center 121 indicates a corneal reflex center in an image in which the eyeball 111 is captured by the second camera 102B. A corneal reflex center 122 indicates a corneal reflex center in an image in which the eyeball 111 is captured by the first camera 102A. A corneal reflex center 124 indicates a corneal reflex center corresponding to the virtual light source 103V.

Positional data of the corneal reflex center 124 is calculated based on positional data of the corneal reflex center 121 and positional data of the corneal reflex center 122 that are captured by the stereo camera device 102. The stereo camera device 102 detects the positional data of the corneal reflex center 121 and the positional data of the corneal reflex center 122 in a three-dimensional local coordinate system that is defined by the stereo camera device 102. The stereo camera device 102 is subjected to camera calibration in advance by a stereo calibration method, and a conversion parameter for converting the three-dimensional local coordinate system of the stereo camera device 102 to a three-dimensional global coordinate system is calculated. The conversion parameter is stored in the storage unit 27. The curvature center calculation unit 25 converts the positional data of the corneal reflex center 121 and the positional data of the corneal reflex center 122 that are captured by the stereo camera device 102 to pieces of positional data in the three-dimensional global coordinate system by using the conversion parameter. The curvature center calculation unit 25 calculates the positional data of the corneal reflex center 124 in the three-dimensional global coordinate system based on the positional data of the corneal reflex center 121 and the positional data of the corneal reflex center 122 that are defined in the three-dimensional global coordinate system.

A corneal curvature center 110 is present on a straight line 123 that connects the virtual light source 103V and the corneal reflex center 124. The curvature center calculation unit 25 calculates, as the position of the corneal curvature center 110, a position at which the distance from the corneal reflex center 124 is equal to a predetermined value on the straight line 123. As the predetermined value, a corneal curvature radius 109 is used. The corneal curvature radius 109 is a distance between a cornea surface and the corneal curvature center 110. As a value of the corneal curvature radius 109, for example, a certain value that is determined in advance from a value of a normal corneal curvature radius or the like may be used.

Meanwhile, when the third light source 103C and the fourth light source 103D are used, the third light source 103C and the fourth light source 103D are arranged such that the first light source 103A and the second light source 103B are located at the same X-coordinate above the display unit 101, and the corneal curvature center 110 is calculated by the same method as described above based on the assumption that a virtual light source 103V2 (not illustrated) is present at an intermediate position between the third light source 103C and the fourth light source 103D.

Line-of-Sight Detection Method

Figure 5:
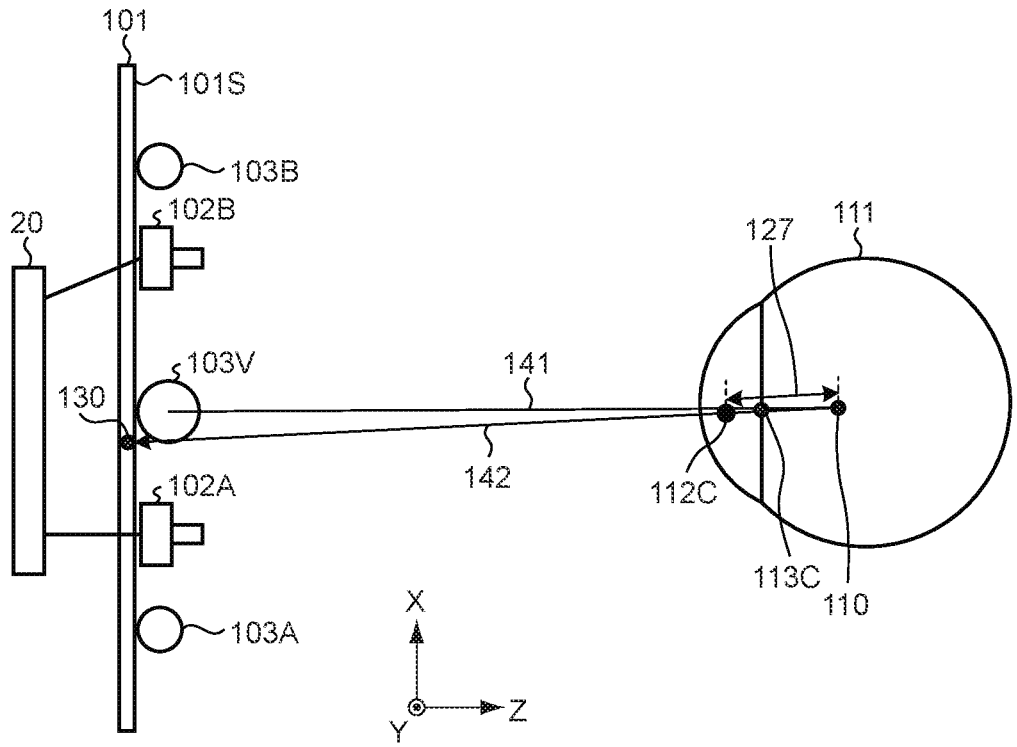
FIG. 5 is a schematic diagram for explaining a principle of a calibration process according to the present embodiment.

In the line-of-sight detection method according to the present embodiment, the calibration process is first performed, and thereafter, a gaze point detection process is performed. First, a principle of the calibration process will be described. FIG. 5 is a schematic diagram for explaining the principle of the calibration process according to the present embodiment. In the calibration process, a target position 130 is set to take attention of the subject. The target position 130 is set in the three-dimensional global coordinate system. The display control unit 21 displays a target image at the set target position 130.

The first light source 103A and the second light source 103B illuminate the eyeball 111. The first camera 102A and the second camera 102B capture images of the eyeball 111. For example, if the first light source 103A emits the detection light, the second camera 102B captures the image of the eyeball 111. Further, if the second light source 103B emits the detection light, the first camera 102A captures the image of the eyeball 111. Meanwhile, when the third light source 103C and the fourth light source 103D are used instead of the first light source 103A and the second light source 103B, the third light source 103C and the fourth light source 103D emit the detection light, and the first camera 102A and the second camera 102B capture images of the eyeball 111 at different timings, for example. The position detection unit 24 detects positional data of a pupil center 112C and positional data of a corneal reflex center 113C based on the image data of the eyeball 111 that is acquired by the image data acquisition unit 23. The position detection unit 24 converts each piece of the detected positional data to the global coordinate system.

When the first light source 103A and the second light source 103B emit the detection light, the curvature center calculation unit 25 calculates the positional data of the corneal curvature center 110 based on positional data of the virtual light source 103V, the positional data of the target position 130, the positional data of the pupil center 112C, and the positional data of the corneal reflex center 113C. Specifically, the curvature center calculation unit 25 calculates a first straight line 141 that connects the virtual light source 103V and the corneal reflex center 113C. Further, when the third light source 103C and the fourth light source 103D emit the detection light, the curvature center calculation unit 25 calculates the positional data of the corneal curvature center 110 based on positional data of the virtual light source 103V2, the positional data of the target position 130, the positional data of the pupil center 112C, and the positional data of the corneal reflex center 113C.

Furthermore, the curvature center calculation unit 25 calculates a second straight line 142 that connects the target position 130 and the pupil center 112C. The curvature center calculation unit 25 calculates an intersection point of the first straight line 141 and the second straight line 142 as the positional data of the corneal curvature center 110. Moreover, the curvature center calculation unit 25 calculates a distance 127 between the corneal curvature center 110 and the pupil center 112C, and stores the distance as calibration data in the storage unit 27. In the present embodiment, a distance (Ra) between the corneal curvature center 110 and the pupil center 112C when the first light source 103A and the second light source 103B emit the detection light and a distance (Rb) between the corneal curvature center 110 and the pupil center 112C when the third light source 103C and the fourth light source 103D emit the detection light are calculated.

Figure 6:
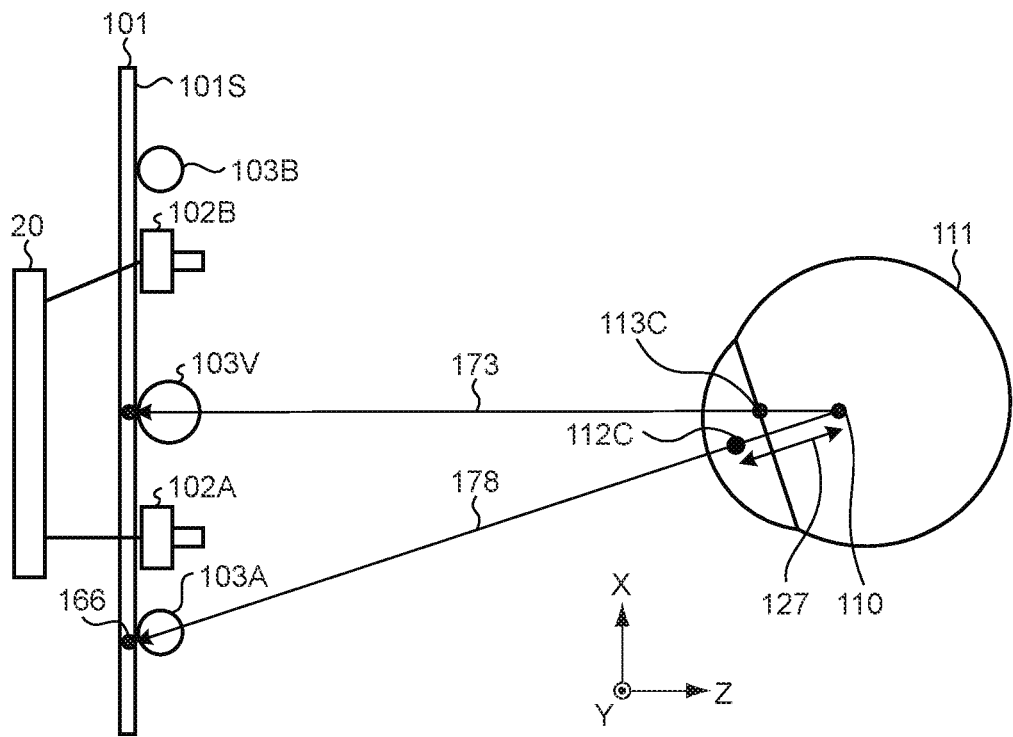
FIG. 6 is a schematic diagram for explaining a principle of a line-of-sight detection process according to the present embodiment.

A principle of a line-of-sight detection process will be described below. FIG. 6 is a schematic diagram for explaining the principle of the line-of-sight detection process according to the present embodiment. In the line-of-sight detection process, similarly to the calibration process, the eyeball 111 is illuminated by using the first light source 103A and the second light source 103B or by using the third light source 103C and the fourth light source 103D. The first camera 102A and the second camera 102B capture images of the eyeball 111. The position detection unit 24 detects the positional data of the pupil center 112C and the positional data of the corneal reflex center 113C based on the image data of the eyeball 111 that is acquired by the image data acquisition unit 23.

When the first light source 103A and the second light source 103B emit the detection light, the curvature center calculation unit 25 calculates the positional data of the corneal curvature center 110 based on the positional data of the virtual light source 103V, the positional data of the pupil center 112C, the positional data of the corneal reflex center 113C, and the distance 127 between the corneal curvature center 110 and the pupil center 112C that is calculated by the calibration process. Specifically, the curvature center calculation unit 25 calculates a straight line 173 that connects the virtual light source 103V and the corneal reflex center 113C. Similarly, when the third light source 103C and the fourth light source 103D emit the detection light, the curvature center calculation unit 25 calculates the positional data of the corneal curvature center 110 based on the positional data corresponding to the virtual light source 103V2, the positional data of the pupil center 112C, the positional data of the corneal reflex center 113C, and the distance 127 between the corneal curvature center 110 and the pupil center 112C that is calculated in the calibration process.

Further, the curvature center calculation unit 25 calculates, as the positional data of the corneal curvature center 110, a position that is separated by a certain distance corresponding to the distance 127 from the pupil center 112C toward the inside of the eyeball 111. The gaze point detection unit 26 calculates a straight line 178 that connects the pupil center 112C and the corneal curvature center 110, and calculates, as the positional data of the gaze point, positional data of an intersection point 166 of the straight line 178 and the display unit 101.

Figure 7:
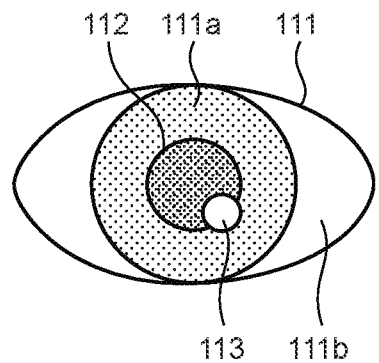
FIG. 7 is a diagram illustrating an example of the eyeball in which a reflected image of detection light is formed.
Figure 7:
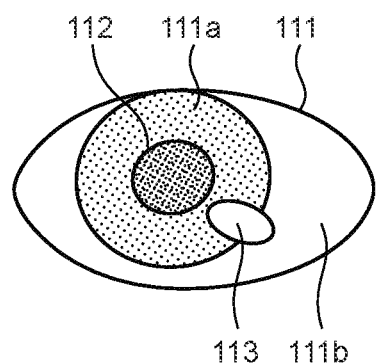
Figure 7:
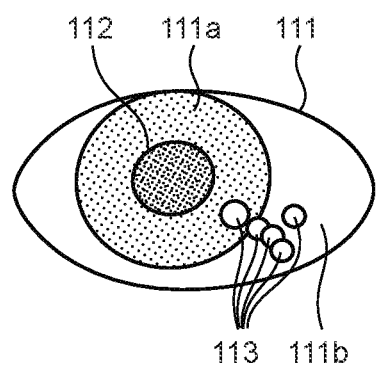

FIG. 7 is a diagram illustrating an example of the eyeball in which the reflected image of the detection light is formed. As illustrated in an upper part in FIG. 7, when the subject looks at a position that is not much separated from the virtual light source 103V, and if the corneal reflex image 113 of the detection light applied to the eyeball 111 of the subject is present on a cornea 111a, the corneal reflex image 113 has a single elliptical shape with a small oblateness for example, so that it is possible to detect the positional data of the corneal reflex center with high accuracy.

As illustrated in a middle part in FIG. 7 and a lower part in FIG. 7, when the subject looks at a position that is largely separated from the virtual light source 103V, the corneal reflex image 113 of the detection light applied to the eyeball 111 of the subject may be present at a boundary between the cornea 111a and a sclera 111b. In this case, due to a difference in a curvature radius and reflectance for example, the corneal reflex image 113 of the detection light is deformed into an elliptical shape with a large oblateness, a long circle, or the like as illustrated in the middle part in FIG. 7 for example, or the plurality of corneal reflex images 113 may be formed as illustrated in the lower part in FIG. 7. Therefore, detection accuracy of the positional data of the corneal reflex center is reduced, so that detection accuracy of a line of sight may be reduced.

In contrast, in the present embodiment, as one example, control of changing the light source for emitting the detection light is performed such that the reflected image of the detection light is formed at a certain position so as not to protrude from the cornea 111a of the subject, based on the target distance between the pupil center and the corneal reflex center of the subject. The position at which the reflected image of the detection light is formed is determined based on, for example, the position of the eyeball of the subject and the positional relationship between the camera and the light source.

Figure 8:
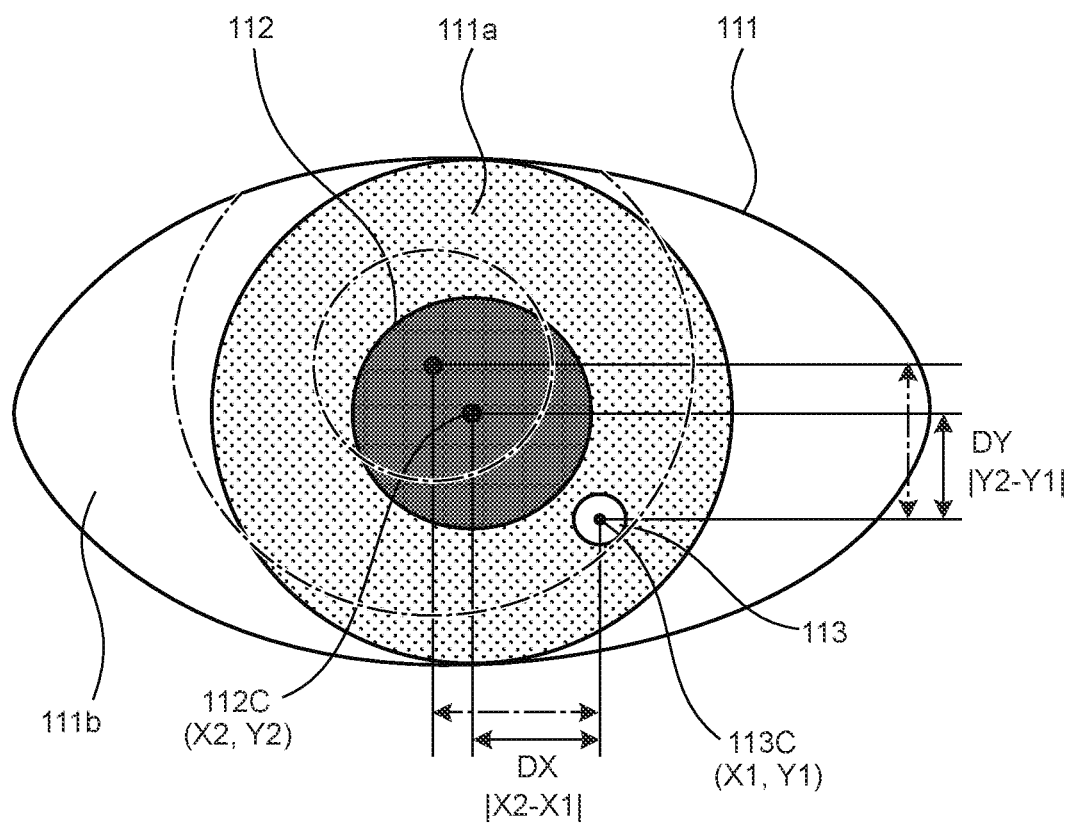
FIG. 8 is a diagram illustrating an example of the eyeball in which the reflected image of the detection light is formed.

FIG. 8 is a diagram illustrating an example of the eyeball in which the reflected image of the detection light is formed. As illustrated in FIG. 8, the light source control unit 22 calculates a target distance between the pupil center 112C and the corneal reflex center 113C that are calculated based on the image data of the eyeball 111. The light source control unit 22 calculates, as the target distance, for example, a distance between the pupil center 112C and the corneal reflex center 113C in each of the vertical direction (Y direction) and the horizontal direction (X direction). Meanwhile, the light source control unit 22 may calculate, as the target distance, a minimum distance between the pupil center 112C and the corneal reflex center 113C. In the following, the distance between the pupil center 112C and the corneal reflex center 113C in the vertical direction will be described as a target distance DY and the distance in the horizontal direction will be described as a target distance DX. In the example illustrated in FIG. 8, a case is illustrated in which the light source control unit 22 calculates the target distance DY and the target distance DX. The light source control unit 22 is able to calculate, as the target distance DY, an absolute value |Y2−Y1| of a difference between a Y coordinate (Y2) of the pupil center 112C and a Y coordinate (Y1) of the corneal reflex center 113C, for example. Furthermore, the light source control unit 22 is able to calculate, as the target distance DX, an absolute value |X2−X1| of a difference between an X coordinate (X2) of the pupil center 112C and an X coordinate (X1) of the corneal reflex center 113C.

In the present embodiment, the positions of the pupil center 112C, the cornea 111a, and the sclera 111b are changed when the subject moves the eyeball 111. Therefore, relative positional relationships among the corneal reflex image 113, the pupil center 112C, the cornea 111a, and the sclera 111b are changed, so that the target distance DY and the target distance DX are changed. For example, when the corneal reflex image 113 is located on a lower right side with respect to the pupil center 112C in the figure as illustrated in FIG. 8, and if the subject moves the eyeball 111 to an opposite side of the corneal reflex image 113 (upper left side: chain lines in the figure), the relative positional relationship between the corneal reflex image 113 and the pupil center 112C and the relative positional relationship between the cornea 111a and the sclera 111b are changed, so that the target distance DY and the target distance DX are increased.

In the present embodiment, thresholds for the target distance DY and the target distance DX are set in advance such that the corneal reflex image 113 is located within the cornea 111a. Meanwhile, the light source control unit 22 may set the thresholds for the target distance DY and the target distance DX in the calibration process. In this case, for example, it may be possible to use, as the thresholds, values of the target distance DY and the target distance DX that are obtained when the subject gazes at a center position of a display screen 1015 of the display unit 101. The light source control unit 22 sets thresholds to be used when the first light source 103A and the second light source 103B emit the detection light and thresholds to be used when the third light source 103C and the fourth light source 103D emit the detection light. Therefore, if the target distance DY exceeds the threshold when the first light source 103A and the second light source 103B emit the detection light, it is possible to determine that the subject gazes at an upper portion relative to the center position of the display screen 1015. Further, if the target distance DY exceeds the threshold when the third light source 103C and the fourth light source 103D emit the detection light, it is possible to determine that the subject gazes at a lower portion relative to the display screen 1015. The light source control unit 22 changes the lighting device 103 for emitting the detection light such that the calculated target distance DY and the calculated target distance DX become smaller than the thresholds that are set in advance. The light source control unit 22 may control change of the lighting device 103 by using only one of the target distance DY and the target distance DX. A case will be described below, as an example, in which the threshold is set for the target distance DY and control is performed such that the target distance DY becomes smaller than the threshold. It is assumed that the threshold for the target distance DY in a case where the first light source 103A and the second light source 103B emit the detection light is denoted by α, and the threshold for the target distance DY in a case where the third light source 103C and the fourth light source 103D emit the detection light is denoted by β. Meanwhile, when change of the lighting device 103 is controlled by using both of the target distance DY and the target distance DX, it may be possible to perform control such that a value of at least one of the target distance DY and the target distance DX becomes smaller than the threshold.

Figure 9:
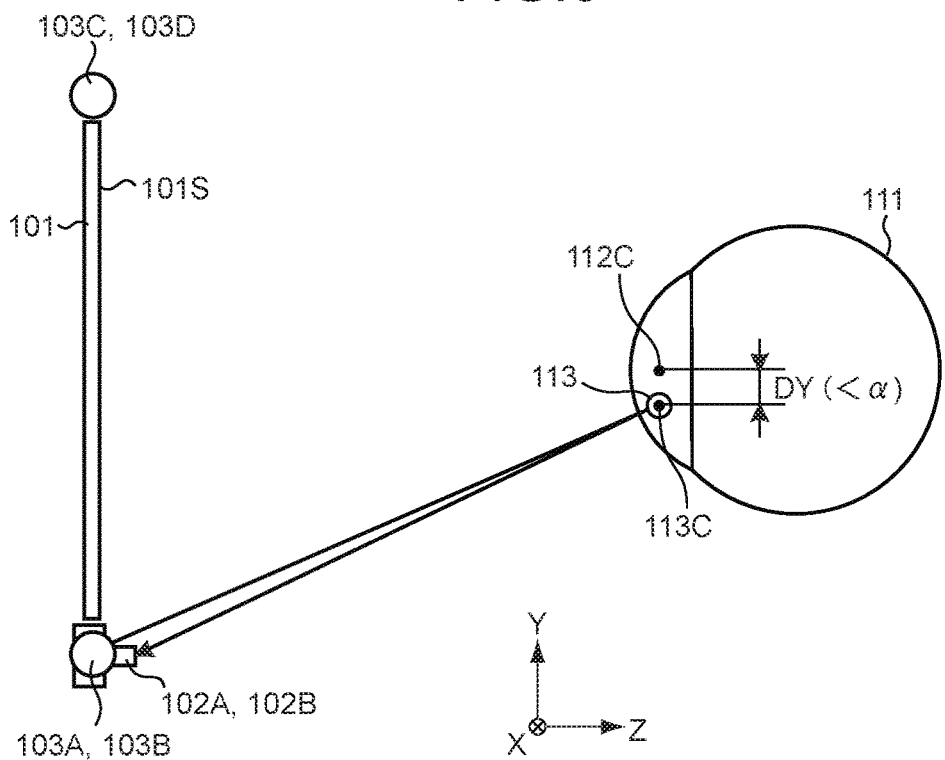
FIG. 9 is a diagram illustrating an example of operation of a lighting device in the line-of-sight detection process.

FIG. 9 to FIG. 13 are diagrams illustrating an example of operation of the lighting device 103 in the line-of-sight detection process. In the line-of-sight detection process, when a gaze point is detected for the first time, for example, the light source control unit 22 causes the first light source 103A and the second light source 103B to emit the detection light. As illustrated in FIG. 9, for example, if the target distance DY between the pupil center 112C and the corneal reflex center 113C in the Y direction in the image data of the eyeball 111 is smaller than the threshold α, the light source control unit 22 causes the first light source 103A and the second light source 103B that serves as the lower light source to emit the detection light.

Figure 10:
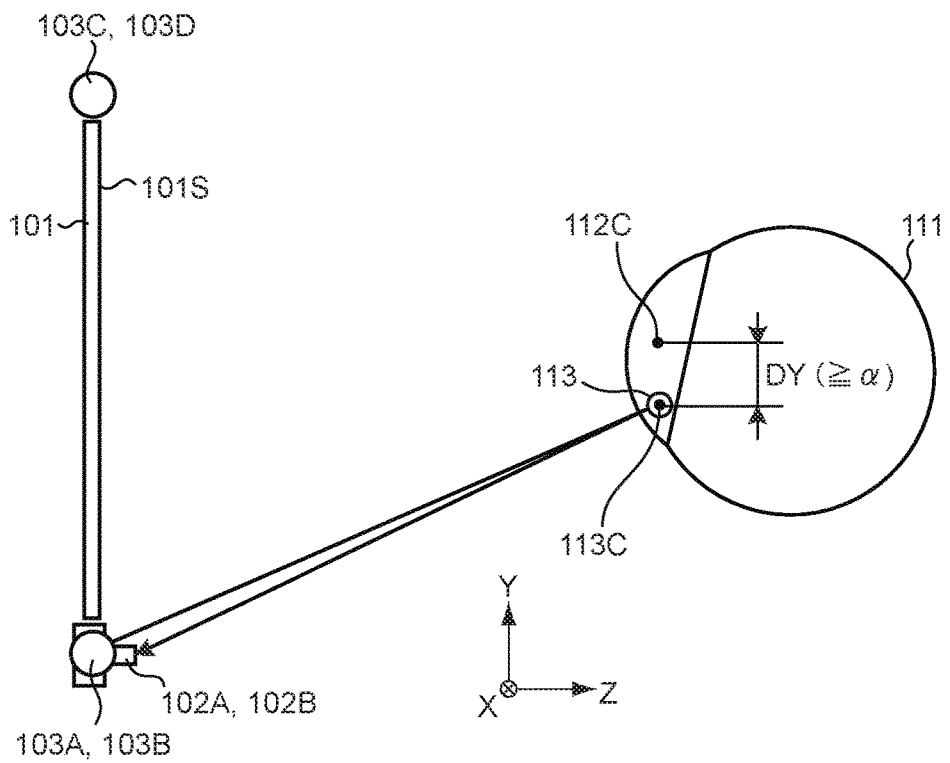
FIG. 10 is a diagram illustrating an example of operation of the lighting device in the line-of-sight detection process.
Figure 11:
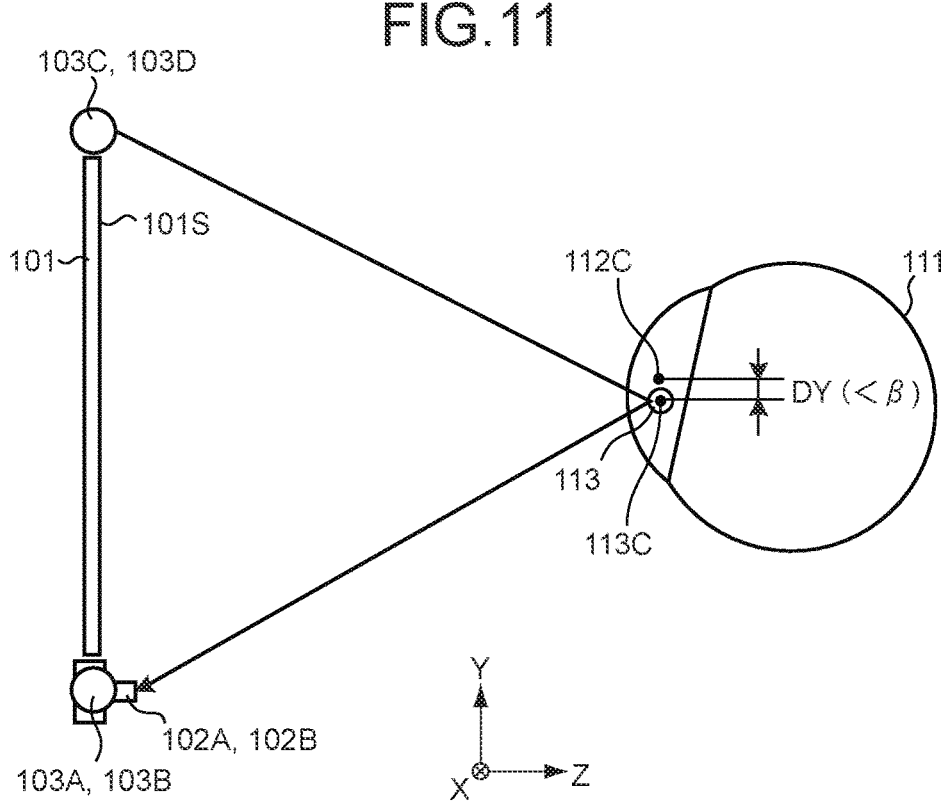
FIG. 11 is a diagram illustrating an example of operation of the lighting device in the line-of-sight detection process.

In contrast, as illustrated in FIG. 10, for example, if the target distance DY between the pupil center 112C and the corneal reflex center 113C in the Y direction in the image data of the eyeball 111 is equal to or larger than the threshold α, the light source control unit 22 changes the light sources such that, as illustrated in FIG. 11, the third light source 103C and the fourth light source 103D that serve as the upper light source emit the detection light.

The light source control unit 22 is able to perform the same control when the third light source 103C and the fourth light source 103D that serve as the upper light source emit the detection light. As illustrated in FIG. 11, for example, if the target distance DY between the pupil center 112C and the corneal reflex center 113C in the Y direction in the image data of the eyeball 111 is smaller than the threshold β, the light source control unit 22 causes the third light source 103C and the fourth light source 103D that serve as the upper light source to emit the detection light.

Figure 12:
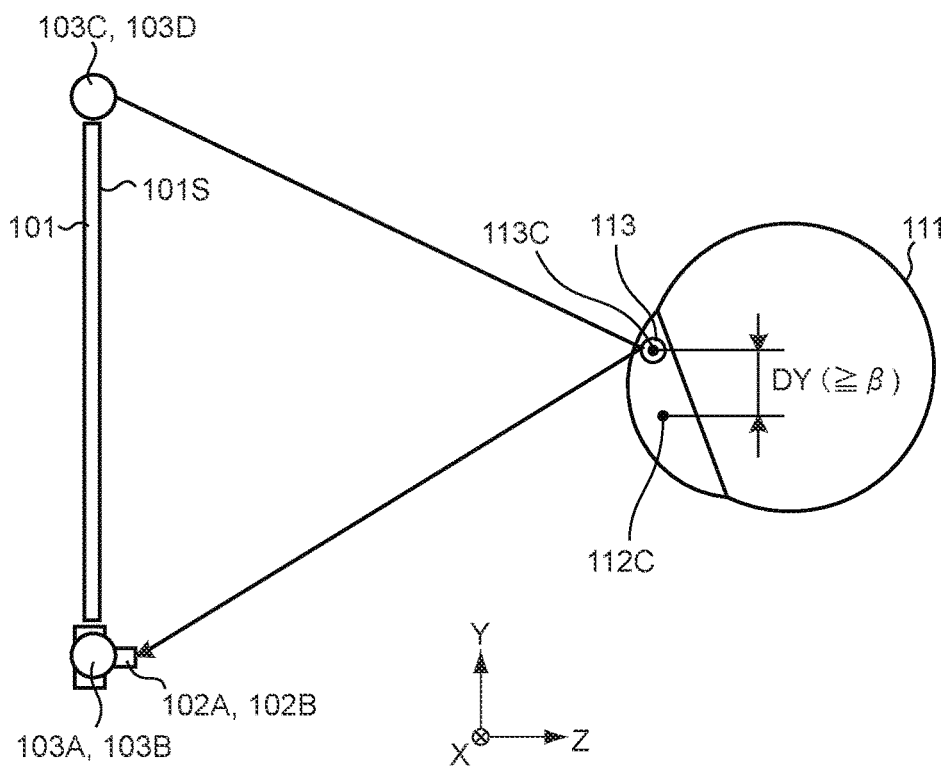
FIG. 12 is a diagram illustrating an example of operation of the lighting device in the line-of-sight detection process.
Figure 13:
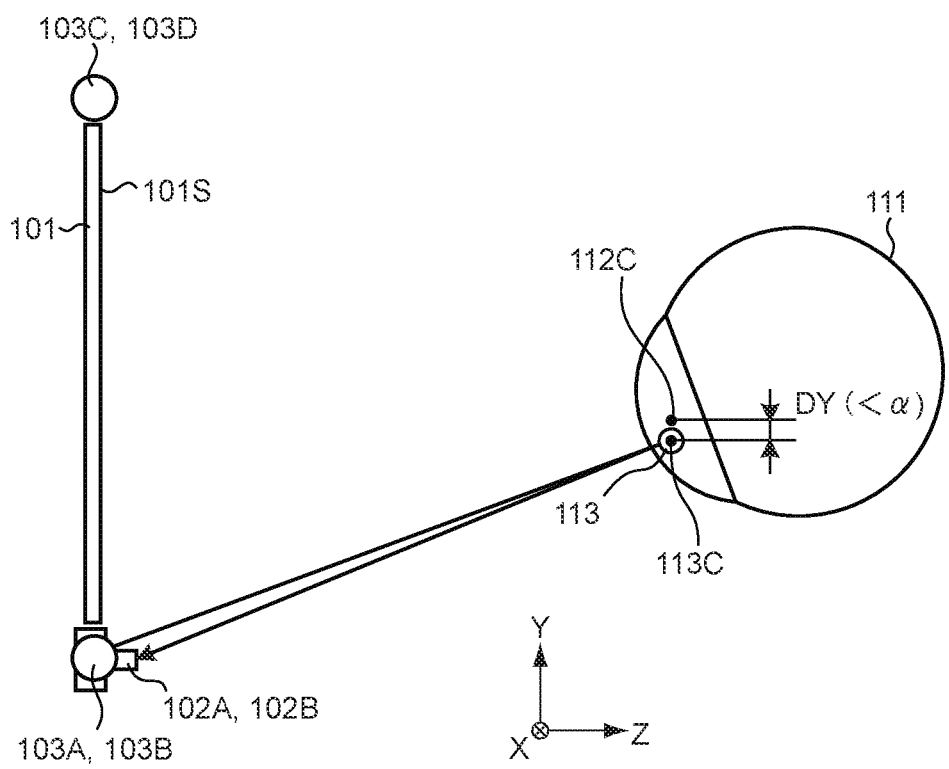
FIG. 13 is a diagram illustrating an example of operation of the lighting device in the line-of-sight detection process.

In contrast, as illustrated in FIG. 12, for example, if the target distance DY between the pupil center 112C and the corneal reflex center 113C in the Y direction in the image data of the eyeball 111 is equal to or larger than the threshold β, the light source control unit 22 changes the light sources such that, as illustrated in FIG. 13, the first light source 103A and the second light source 103B that serve as the lower light source emit the detection light.

The light source control unit 22 causes one of the first light source 103A and the second light source 103B that serve as the lower light source to emit light and apply the detection light to the eyeball 111, and causes one of the first camera 102A and the second camera 102B that is located more distant from the light source that has emitted the light than the other one of the first camera 102A and the second camera 102B to capture an image of the eyeball 111 of the subject. Thereafter, the other one of the first light source 103A and the second light source 103B is caused to emit light and apply the detection light to the eyeball 111, and one of the first camera 102A and the second camera 102B that is located more distant from the light source hat has emitted the light than the other one of the first camera 102A and the second camera 102B to capture an image of the eyeball 111 of the subject. For example, when the first light source 103A emits the detection light, the second camera 102B captures the image of the eyeball 111. Further, when the second light source 103B emits the detection light, the first camera 102A captures the image of the eyeball 111.

Similarly, the light source control unit 22 causes one of the third light source 103C and the fourth light source 103D that serve as the upper light source to emit light and apply the detection light to the eyeball 111, and causes one of the first camera 102A and the second camera 102B that is located more distant from the light source hat has emitted the light than the other one of the first camera 102A and the second camera 102B to capture an image of the eyeball 111 of the subject. Thereafter, the other one of the third light source 103C and the fourth light source 103D is caused to emit light and apply the detection light to the eyeball 111, and the camera that is located more distant from the light sources that has emitted light among the first camera 102A and the second camera 102B to capture an image of the eyeball 111 of the subject. For example, when the third light source 103C emits the detection light, the second camera 102B captures the image of the eyeball 111. Further, when the fourth light source 103D emits the detection light, the first camera 102A captures the image of the eyeball 111.

The image data acquisition unit 23 acquires the image data. The position detection unit 24 detects the positional data of the pupil center and the positional data of the corneal reflex center based on the acquired image data. The position detection unit 24 determines whether the positional data of the corneal reflex center is normally detected. If the reflected image of the detection light is located within the cornea of the subject, the possibility that a normal value is detected increases. In contrast, if the reflected image of the detection light is not located within the cornea of the subject and is deformed while protruding on the sclera for example, the possibility that the normal value is detected decreases. If the normal value is detected, the positional data of the gaze point is acquired by processes performed by the curvature center calculation unit 25 and the gaze point detection unit 26. Meanwhile, if the normal value is not detected, the gaze point detection unit 26 may determine, for example, an error in the line-of-sight detection process.

If the normal value of the corneal reflex center is detected, the curvature center calculation unit 25 calculates the corneal curvature center based on the detected value. In this case, when the lower light source (the first light source 103A and the second light source 103B) serves as the light source for emitting the detection light in the line-of-sight detection process, the curvature center calculation unit 25 calculates the corneal curvature center by using a value of the distance Ra, which is calculated when the lower light source serves as the light source for emitting the detection light, from the two different distances (the distances between the corneal curvature center and the pupil center) Ra and Rb that are calculated in the calibration process. Further, when the upper light source (the third light source 103C and the fourth light source 103D) serves as the light source for emitting the detection light in the line-of-sight detection process, the curvature center calculation unit 25 calculates the corneal curvature center by using a value of the distance Rb that is calculated when the upper light source serves as the light source for emitting the detection light in the calibration process.

Figure 14:
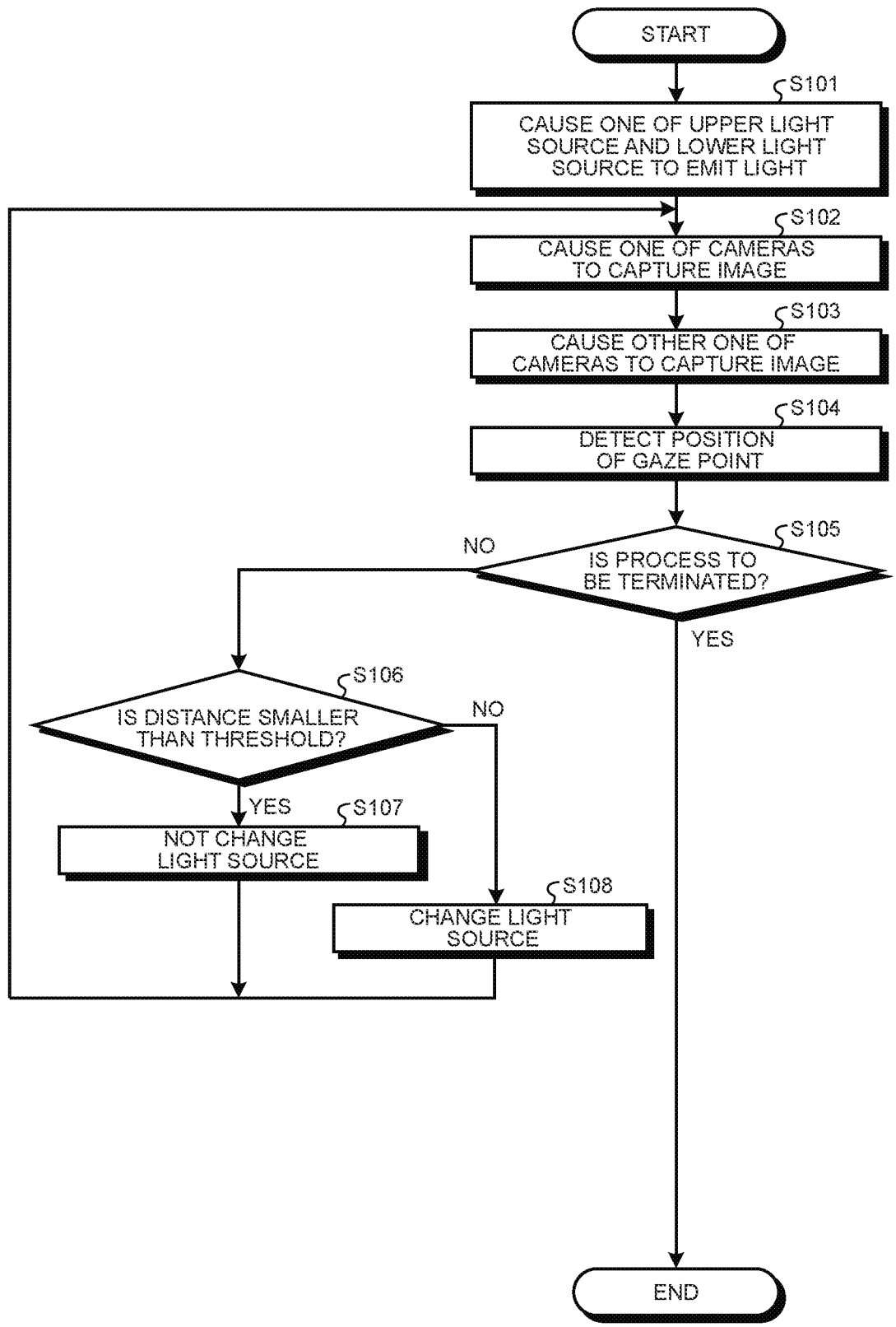
FIG. 14 is a flowchart illustrating an example of the line-of-sight detection process in a line-of-sight detection method according to the present embodiment.

An example of the line-of-sight detection method according to the present embodiment will be described below with reference to FIG. 14. FIG. 14 is a flowchart illustrating an example of the line-of-sight detection process in the line-of-sight detection method according to the present embodiment. As illustrated in FIG. 14, in the line-of-sight detection process, the light source control unit 22 causes one of the lower light source (the first light source 103A and the second light source 103B) and the upper light source (the third light source 103C and the fourth light source 103D) to emit the detection light (Step S101). In this case, the light source control unit 22 performs control of causing one of the first light source 103A and the second light source 103B to emit light and apply the detection light to the eyeball 111, and causing one of the first camera 102A and the second camera 102B that is located more distant from the light source that has emitted the light than the other one of the first camera 102A and the second camera 102B to capture an image of the eyeball 111 of the subject (Step S102). Further, the light source control unit 22 performs control of causing the other one of the first light source 103A and the second light source 103B to emit light and apply the detection light to the eyeball 111, and causing one of the first camera 102A and the second camera 102B that is located more distant from the light source that has emitted the light than the other one of the first camera 102A and the second camera 102B to capture an image of the eyeball 111 of the subject (Step S103). For example, when the first light source 103A emits the detection light, the second camera 102B captures the image of the eyeball 111. Further, when the second light source 103B emits the detection light, the first camera 102A captures the image of the eyeball 111.

The image data acquisition unit 23 acquires the image data. The position detection unit 24 detects the positional data of the pupil center and the corneal reflex center based on the acquired image data. Thereafter, the positional data of the gaze point is acquired by processes performed by the curvature center calculation unit 25 and the gaze point detection unit 26 (Step S104). At Step S104, when the lower light source (the first light source 103A and the second light source 103B) serves as the light source for emitting the detection light in the line-of-sight detection process, the curvature center calculation unit 25 calculates the corneal curvature center by using a value of the distance Ra that is calculated when the lower light source serves as the light source for emitting the detection light in the calibration process. Further, when the upper light source (the third light source 103C) serves as the light source for emitting the detection light in the line-of-sight detection process, the curvature center calculation unit 25 calculates the corneal curvature center by using a value of the distance Rb that is calculated when the upper light source serves as the light source for emitting the detection light in the calibration process. Meanwhile, if a normal value is not detected at Step S104, it may be possible to determine an error and terminate the process.

After Step S104, the gaze point detection unit 26 determines whether to terminate detection of the gaze point (Step S105). As a result of the determination at Step S105, if the detection of the gaze point is to be terminated (Yes at Step S105), the process is terminated. Further, if the detection of the gaze point is not to be terminated (No at Step S105), the light source control unit 22 determines whether the target distance between the pupil center 112C and the corneal reflex center 113C in the image data of the eyeball 111 is smaller than the threshold (Step S106). If it is determined that the target distance between the pupil center 112C and the corneal reflex center 113C is smaller than the threshold (Yes at Step S106), the light source control unit 22 does not change the light source for emitting the detection light between the lower light source and the upper light source, and repeats the processes from Step S102 (Step S107). In contrast, if it is determined that the target distance between the pupil center 112C and the corneal reflex center 113C is not smaller than the threshold, the light source control unit 22 changes the light source for emitting the detection light between the lower light source and the upper light source, and repeats the processes from Step S102 (Step S108).

Another example of control of changing the light source for emitting the detection light in the present embodiment will be described below. In the following, a case will be described as an example in which control of changing the light source for emitting the detection light is performed based on whether the shape of the corneal reflex image 113 of the detection light in the image data of the eyeball 111 is included in the reference shape.

Figure 15:
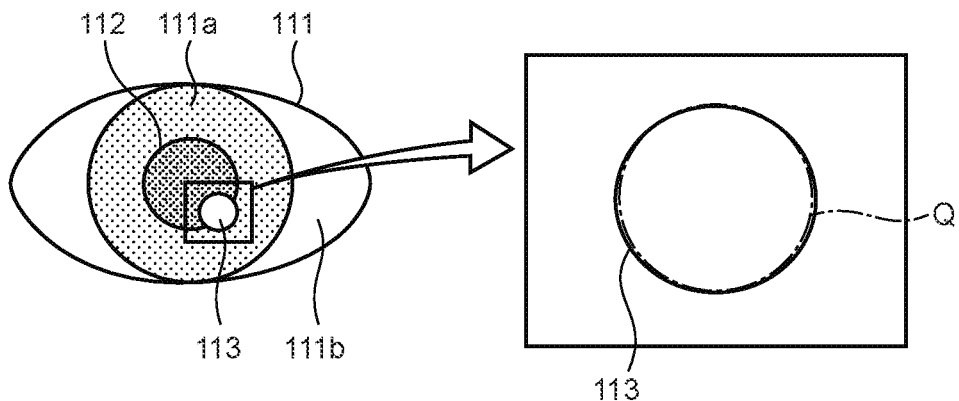
FIG. 15 is a diagram illustrating another example of the eyeball in which the reflected image of the detection light is formed.
Figure 15:
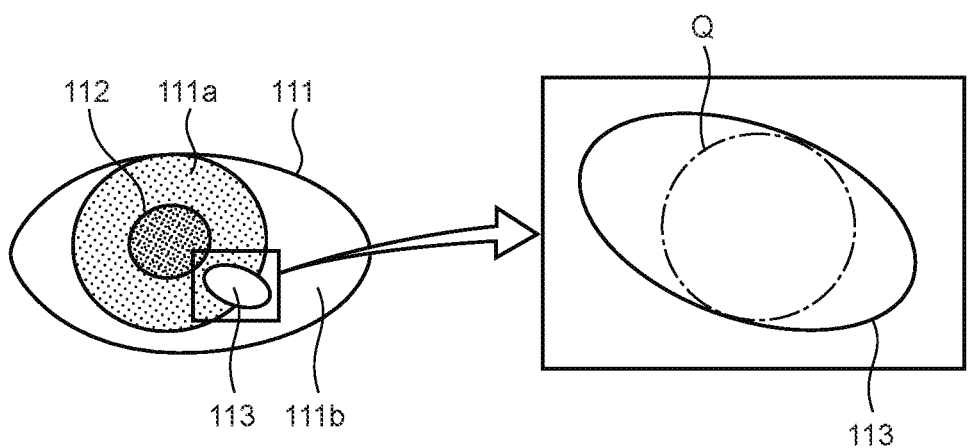
Figure 15:
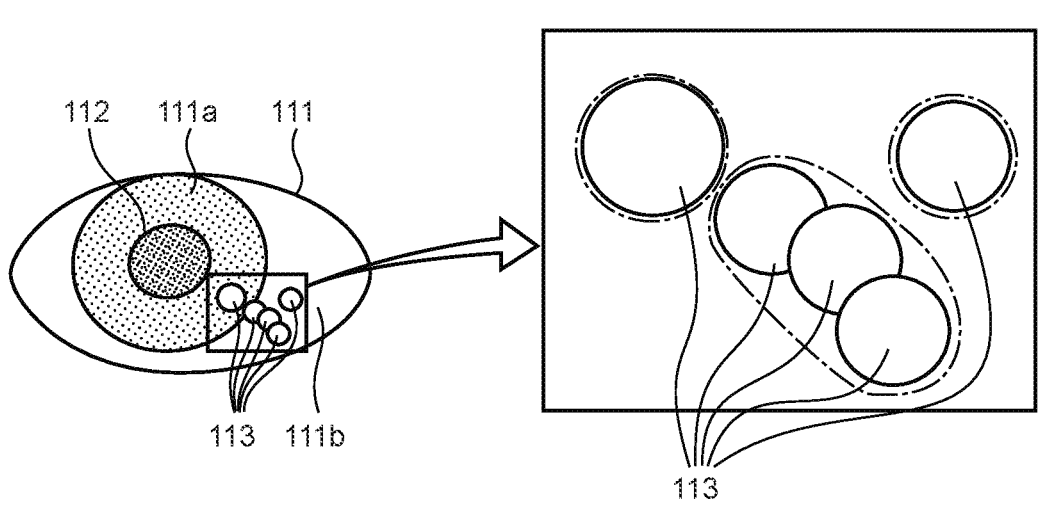

FIG. 15 is a diagram illustrating another example of the eyeball in which the reflected image of the detection light is formed. As indicated in an upper part in FIG. 15, when the corneal reflex image 113 of the detection light applied to the eyeball 111 of the subject is located on the cornea 111a, the shape of the corneal reflex image 113 is a single elliptical shape with a small oblateness, for example. Therefore, in the present embodiment, it is possible to adopt a single elliptical shape with an oblateness smaller than a threshold as the reference shape. As for the predetermined value, for example, it may be possible to calculate values in advance based on the assumption that the corneal reflex image 113 is present on the cornea 111a and adopt an average value or a minimum value of calculation results, but embodiments are not limited to this example. When the corneal reflex image 113 of the detection light applied to the eyeball 111 of the subject is present on the cornea 111a, the shape of the corneal reflex image 113 is included in the reference shape. The reference shape may be stored in, for example, the storage unit 27.

In contrast, when the corneal reflex image 113 of the detection light applied to the eyeball 111 of the subject is present at the boundary between the cornea 111a and the sclera 111b, the corneal reflex image 113 of the detection light is deformed into an elliptical shape with a large oblateness, a long circle, or the like as illustrated in a middle part in FIG. 15 for example, or the plurality of corneal reflex images 113 may be formed as illustrated in the lower part in FIG. 15. In other words, when the corneal reflex image 113 of the detection light applied to the eyeball 111 of the subject is present at the boundary between the cornea 111a and the sclera 111b, the shape of the corneal reflex image 113 is not included in the reference shape.

In view of the above, the light source control unit 22 performs image processing on the image data of the eyeball 111, and calculates the shape of the corneal reflex image 113 of the detection light. For example, the light source control unit 22 calculates a region in which luminance exceeds a predetermined value in the image data as a region of the corneal reflex image 113. The light source control unit 22 calculates the number of calculated regions of the corneal reflex image 113. If the calculation result indicates two or more, the light source control unit 22 is able to determine that the shape of the corneal reflex image 113 is not included in the reference shape.

Further, if the calculation result indicates one, the light source control unit 22 determines the shape of the calculated corneal reflex image 113. The light source control unit 22 compares, for example, the calculated corneal reflex image 113 and a reference shape Q, and if a match percentage is equal to or larger than a predetermined value, it is possible to determine that the shape of the corneal reflex image 113 is included in the reference shape. In contrast, the light source control unit 22 compares the calculated corneal reflex image 113 and the reference shape Q, and if the match percentage is smaller than the predetermined value, it is possible to determine that the shape of the corneal reflex image 113 is not included in the reference shape.

When determining that the shape of the corneal reflex image 113 is not included in the reference shape, the light source control unit 22 changes the light source for emitting the detection light between the lower light source (the first light source 103A and the second light source 103B) and the upper light source (the third light source 103C and the fourth light source 103D). In contrast, when determining that the shape of the corneal reflex image 113 is included in the reference shape, the light source control unit 22 does not change the light source for emitting the detection light.

Figure 16:
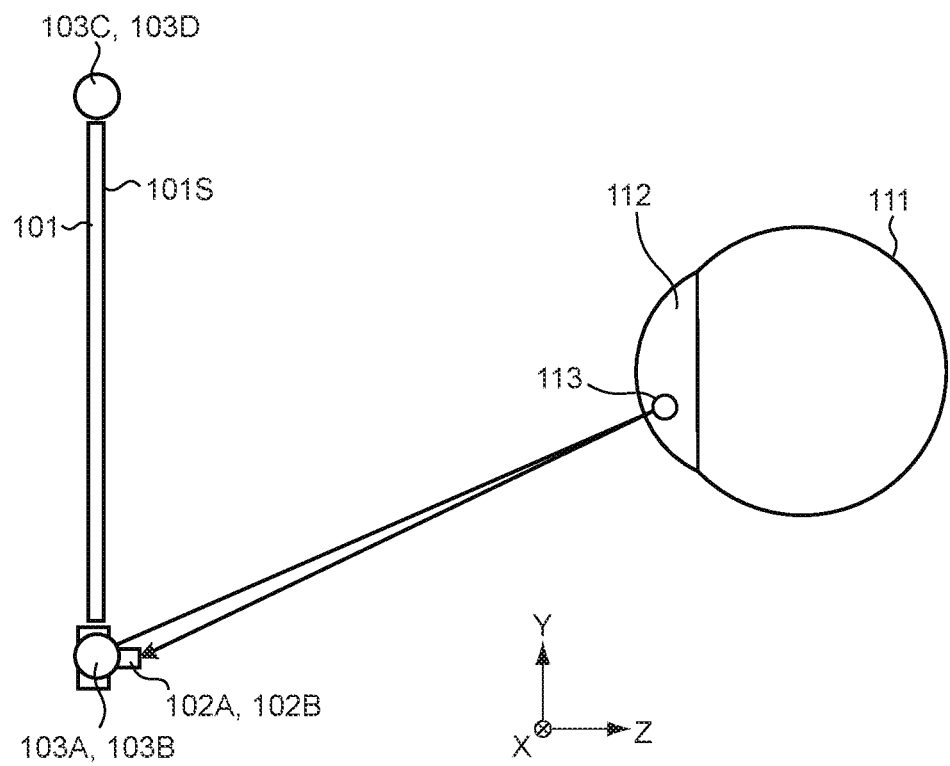
FIG. 16 is a diagram illustrating another example of operation of the lighting device in the line-of-sight detection process.
Figure 17:
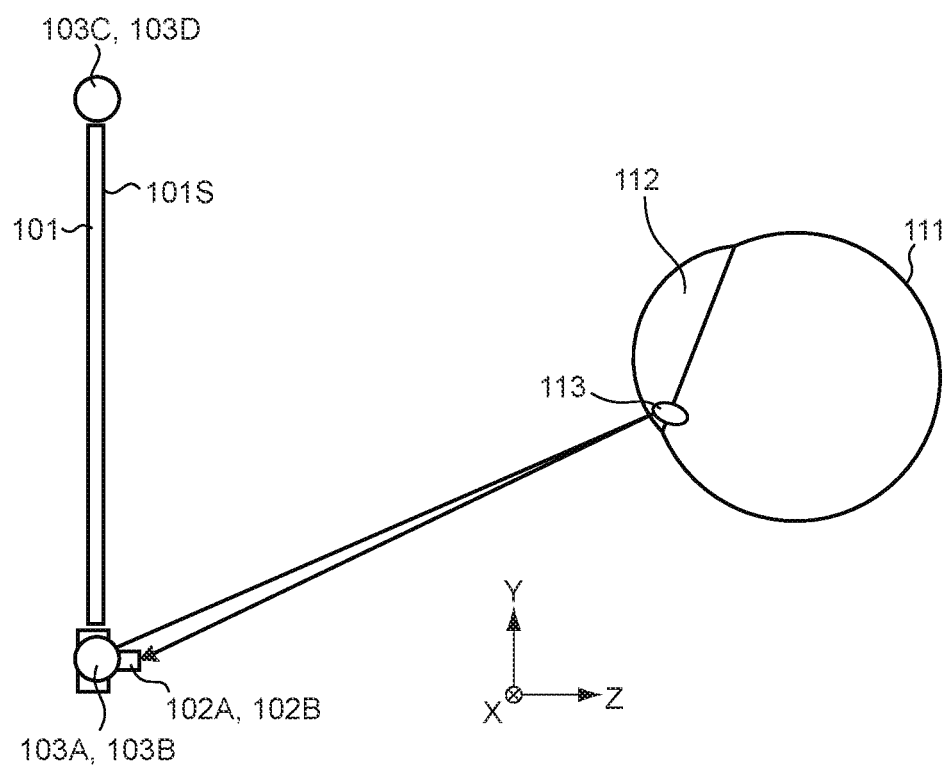
FIG. 17 is a diagram illustrating another example of operation of the lighting device in the line-of-sight detection process.
Figure 18:
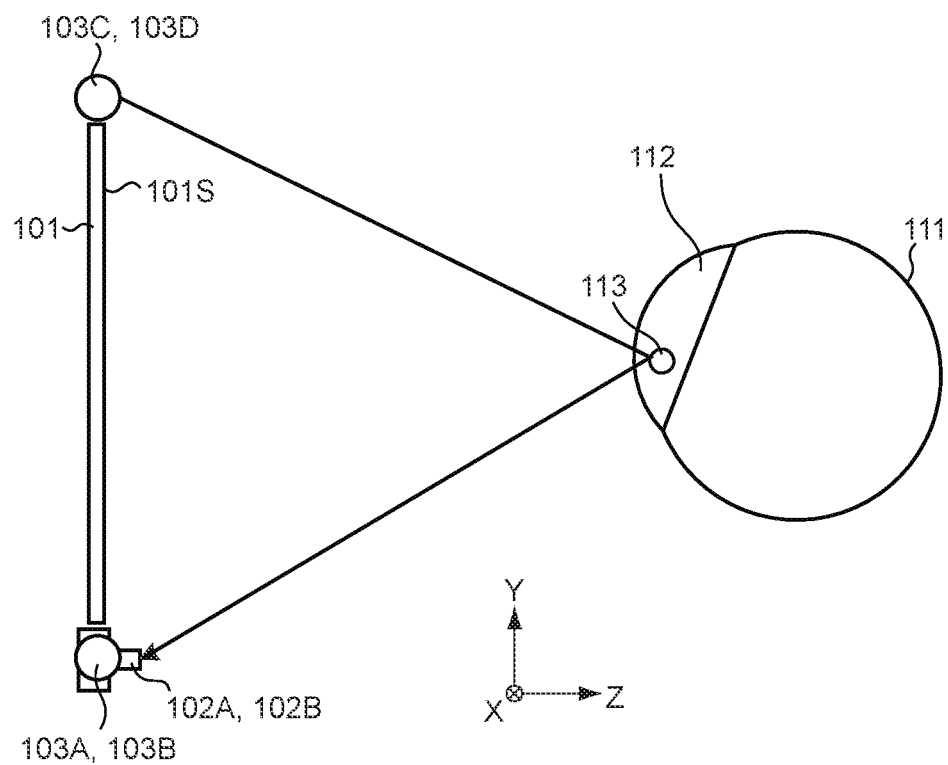
FIG. 18 is a diagram illustrating another example of operation of the lighting device in the line-of-sight detection process.

FIG. 16 to FIG. 18 are diagrams illustrating another example of operation of the lighting device 103 in the line-of-sight detection process. The light source control unit 22 causes the first light source 103A and the second light source 103B to emit the detection light. For example, it is determined whether the shape of the corneal reflex image 113 of the detection light in the image data of the eyeball 111 is included in the reference shape.

When determining that the shape of the corneal reflex image 113 is included in the reference shape, as illustrated in FIG. 16, the light source control unit 22 does not change the light source for emitting the detection light. In contrast, as illustrated in FIG. 17, for example, when determining that the shape of the corneal reflex image 113 is not included in the reference shape, the light source control unit 22 changes the light source such that, as illustrated in FIG. 18, the third light source 103C and the fourth light source 103D that serve as the upper light source emit the detection light.

Figure 19:
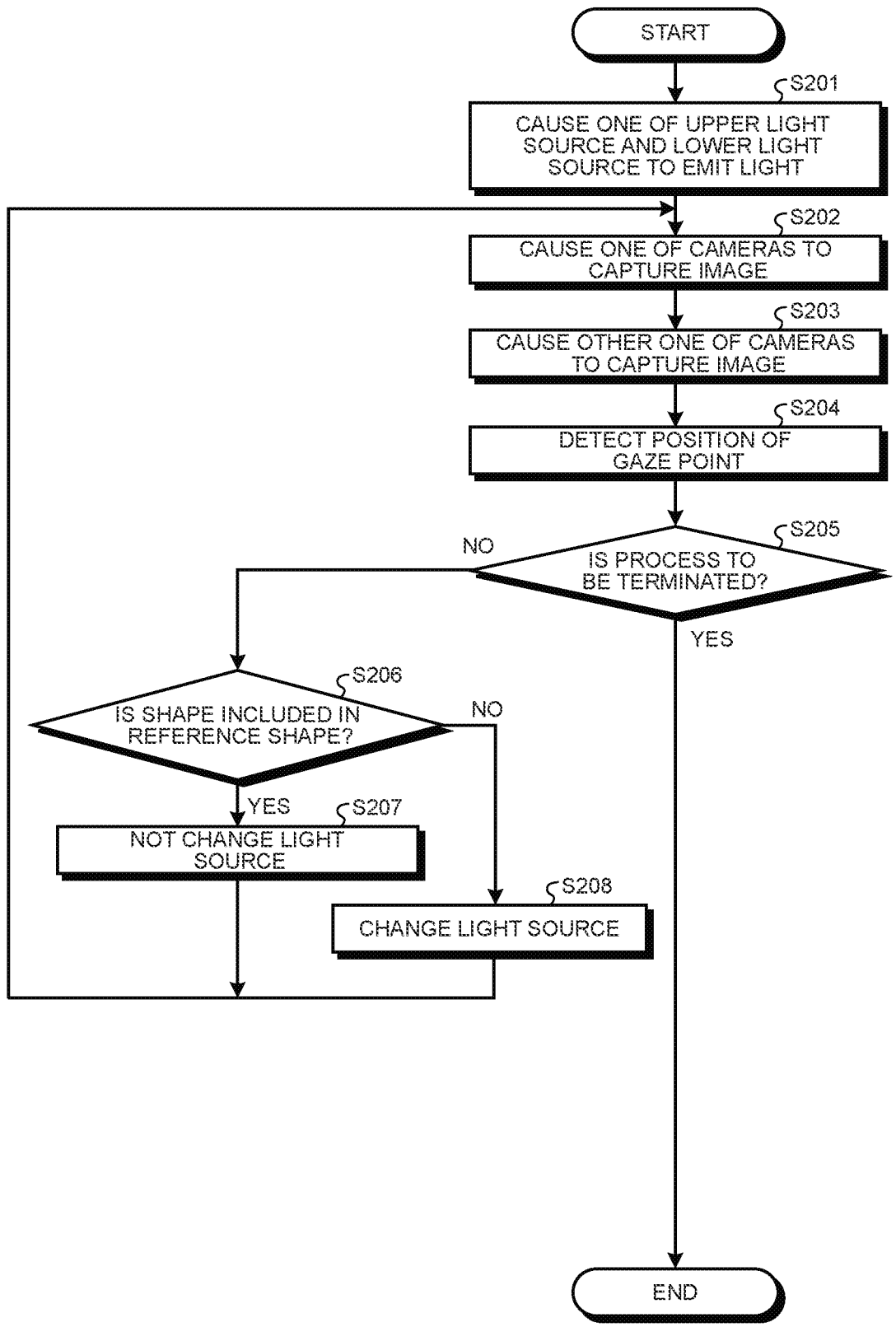
FIG. 19 is a flowchart illustrating another example of the line-of-sight detection process in the line-of-sight detection method according to the present embodiment.

FIG. 19 is a flowchart illustrating another example of the line-of-sight detection process in the line-of-sight detection method according to the present embodiment. As illustrated in FIG. 19, processes from Step S201 to Step S205 are the same as the processes from Step S101 to Step S105 (see FIG. 14) at which the control of changing the light source for emitting the detection light is performed based on the target distance between the pupil center and the corneal reflex center of the subject as described above.

As a result of the determination at Step S205, if the detection of the gaze point is to be terminated (Yes at Step S205), the process is terminated. Further, if the detection of the gaze point is not to be terminated (No at Step S205), the light source control unit 22 determines whether the shape of the corneal reflex image 113 in the image data of the eyeball 111 is included in the reference shape (Step S206). If it is determined that the shape of the corneal reflex image 113 is included in the reference shape (Yes at Step S206), the light source control unit 22 does not change the light source for emitting the detection light between the lower light source and the upper light source, and repeats the processes from Step S202 (Step S207). In contrast, if it is determined that the shape of the corneal reflex image 113 is not included in the reference shape, the light source control unit 22 changes the light source for emitting the detection light between the lower light source and the upper light source and repeats the processes from Step S102 (Step S208).

Figure 20:
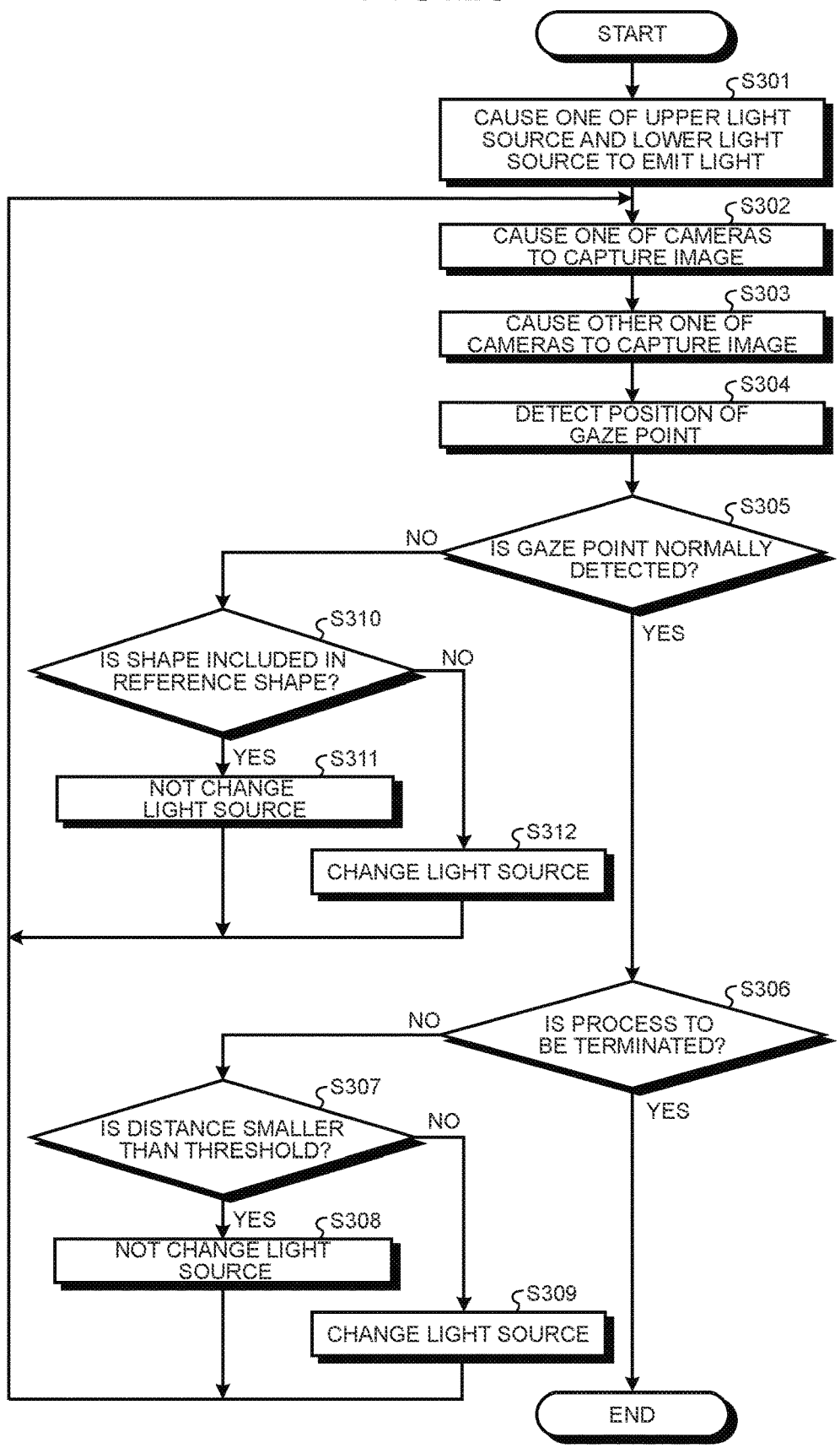
FIG. 20 is a flowchart illustrating still another example of the line-of-sight detection process in the line-of-sight detection method according to the present embodiment.

FIG. 20 is a flowchart illustrating another example of the line-of-sight detection process in the line-of-sight detection method according to the present embodiment. In the example illustrated in FIG. 20, a case is illustrated in which the control of changing the light source for emitting the detection light based on the target distance between the pupil center and the corneal reflex center of the subject and the control of changing the light source for emitting the detection light based on whether the shape of the corneal reflex image 113 is included in the reference shape are combined.

As illustrated in FIG. 20, processes from Step S301 to Step S304 are the same as the processes from Step S101 (S201) to Step S104 (S204) in each control as described above (see FIG. 14 and FIG. 19).

After Step S304, the gaze point detection unit 26 determines whether the gaze point is normally detected (Step S305). At Step S305, if it is determined that the gaze point is normally detected (Yes at Step S305), the gaze point detection unit 26 and the light source control unit 22 perform processes from Step S306 to Step S309. The processes from Step S306 to Step S309 are the same as the processes from Step S105 to Step S108 at which the control of changing the light source for emitting the detection light is performed based on the target distance between the pupil center and the corneal reflex center of the subject (see FIG. 14).

In contrast, at Step S305, if it is determined that the gaze point is not normally detected (No at Step S305), the light source control unit 22 performs processes from Step S310 to Step S312. The processes from Step S310 to Step S312 are the same as the processes from Step S206 to Step S208 at which the control of changing the light source for emitting the detection light is performed based on whether the shape of the corneal reflex image 113 is included in the reference shape (see FIG. 19).

As for the control of changing the light source for emitting the detection light based on the target distance between the pupil center and the corneal reflex center of the subject, the control may be performed based on normal values of the position of the pupil center and the position of the corneal reflex center when the normal values are calculated as the position of the pupil center and the position of the corneal reflex center, that is, when the position of the gaze point is normally detected. In contrast, as for the control of changing the light source for emitting the detection light based on whether the shape of the corneal reflex image 113 is included in the reference shape, the control may be performed based on the shape of the corneal reflex image 113 without calculating the position of the pupil center and the position of the corneal reflex center. Therefore, even if the normal values are not obtained as the position of the pupil center and the position of the corneal reflex center, it is possible to appropriately change the light source for emitting the detection light.

As described above, the line-of-sight detection device 100 according to the present embodiment includes the display unit 101 that displays an image, a plurality of light sources (the first light source 103A, the second light source 103B, the third light source 103C, and the fourth light source 103D) that emit the detection light and apply the detection light to at least one of the eyeballs 111 of the subject, the stereo camera device 102 that captures an image of the eyeball 111 to which the detection light is applied, the position detection unit 24 that detects, from the captured image, the position of the pupil center that indicates the center of the pupil of the eyeball 111 to which the detection light is applied and the position of the corneal reflex center that indicates the center of the corneal reflex, the gaze point detection unit 26 that calculates the position of the gaze point of the subject based on the position of the pupil center and the position of the corneal reflex center, and the light source control unit 22 that changes the light source for emitting the detection light among the plurality of light sources based on the target distance between the pupil center and the corneal reflex center.

Furthermore, the line-of-sight detection method according to the present embodiment includes displaying an image on the display unit 101, emitting, by a plurality of light sources, the detection light and applying the detection light to at least one of the eyeballs 111 of the subject, capturing an image of the eyeball 111 to which the detection light is applied, detecting, from the captured image, the position of the pupil center that indicates the center of the pupil of the eyeball 111 to which the detection light is applied and the position of the corneal reflex center that indicates the center of the corneal reflex, calculating the position of the gaze point of the subject based on the position of the pupil center and the position of the corneal reflex center, and changing the light source for emitting the detection light among the plurality of light sources based on the target distance between the pupil center and the corneal reflex center.

Moreover, the line-of-sight detection program according to the present embodiment causes a computer to execute a process of displaying an image on the display unit 101, a process of emitting, by a plurality of light sources, the detection light and applying the detection light to at least one of the eyeballs 111 of the subject, a process of capturing an image of the eyeball 111 to which the detection light is applied, a process of detecting, from the captured image, the position of the pupil center that indicates the center of the pupil of the eyeball 111 to which the detection light is applied and the position of the corneal reflex center that indicates the center of the corneal reflex, a process of calculating the position of the gaze point of the subject based on the position of the pupil center and the position of the corneal reflex center, and a process of changing the light source for emitting the detection light among the plurality of light sources based on the target distance between the pupil center and the corneal reflex center.

According to the configuration of the present embodiment, it is possible to change the light source for emitting the detection light among the plurality of light sources based on the target distance between the pupil center and the corneal reflex center, so that it is possible to prevent the reflected image of the detection light applied to the eyeball of the subject from being located outside the cornea. Therefore, it is possible to prevent reduction in detection accuracy of the line of sight.

In the line-of-sight detection device 100 according to the present embodiment, the plurality of light sources include the first light source 103A and the second light source 103B that are arranged below the display unit 101 and the third light source 103C and the fourth light source 103D that are arranged above the display unit 101, the distance is the target distance DY in the vertical direction, and the light source control unit 22 changes the light source for emitting the detection light between the lower light source and the upper light source. With this configuration, the light source for emitting the detection light is changed between the lower light source and the upper light source based on the target distance DY in the vertical direction, so that it is possible to infallibly arrange the reflected image of the detection light in the cornea of the subject.

In the line-of-sight detection device 100 according to the present embodiment, the light source control unit 22 changes the light source for emitting the detection light based on whether the shape of the corneal reflex image 113 of the detection light in the image of the eyeball 111 is included in the reference shape. Therefore, even when the position of the pupil center and the position of the corneal reflex center are not obtained, it is possible to appropriately change the light source for emitting the detection light.

Furthermore, the line-of-sight detection device 100 according to the present embodiment includes the display unit 101 that displays an image, a plurality of light sources (the first light source 103A, the second light source 103B, the third light source 103C, and the fourth light source 103D) that emit the detection light and applies the detection light to at least one of the eyeballs 111 of a subject, the stereo camera device 102 that captures an image of the eyeball 111 to which the detection light is applied, the position detection unit 24 that detects, from the captured image, the position of the pupil center that indicates the center of the pupil of the eyeball 111 to which the detection light is applied and the position of the corneal reflex center that indicates the center of the corneal reflex, the gaze point detection unit 26 that calculates the position of the gaze point of the subject based on the position of the pupil center and the position of the corneal reflex center, and the light source control unit 22 that changes the light source for emitting the detection light among the plurality of light sources based on whether the shape of the corneal reflex image 113 of the detection light in the image of the eyeball 111 is included in the reference shape.

Moreover, the line-of-sight detection method according to the present embodiment includes displaying an image, emitting, from a plurality of light sources, the detection light and applying the detection light to at least one of the eyeballs 111 of a subject, capturing an image of the eyeball 111 to which the detection light is applied, detecting, from the captured image, the position of the pupil center that indicates the center of the pupil of the eyeball 111 to which the detection light is applied and the position of the corneal reflex center that indicates the center of the corneal reflex, calculating the position of the gaze point of the subject based on the position of the pupil center and the position of the corneal reflex center, and changing the light source for emitting the detection light among the plurality of light sources based on whether the shape of the corneal reflex image 113 of the detection light in the image of the eyeball 111 is included in the reference shape.

Furthermore, the line-of-sight detection program according to the present embodiment causes a computer to perform a process of displaying an image, a process of emitting, from a plurality of light sources, the detection light and applying the detection light to at least one of the eyeballs 111 of a subject, a process of capturing an image of the eyeball 111 to which the detection light is applied, a process of detecting, from the captured image, the position of the pupil center that indicates the center of the pupil of the eyeball 111 to which the detection light is applied and the position of the corneal reflex center that indicates the center of the corneal reflex, a process of calculating the position of the gaze point of the subject based on the position of the pupil center and the position of the corneal reflex center, and a process of changing the light source for emitting the detection light among the plurality of light sources based on whether the shape of the corneal reflex image 113 of the detection light in the image of the eyeball 111 is included in the reference shape.

According to the configuration of the present embodiment, it is possible to change the light source for emitting the detection light among the plurality of light sources based on whether the shape of the corneal reflex image 113 of the detection light in the image of the eyeball 111 is included in the reference shape, so that it is possible to prevent the reflected image of the detection light applied to the eyeball of the subject from being located outside the cornea. With this configuration, it is possible to prevent reduction in the detection accuracy of the line of sight.

In the line-of-sight detection device 100 according to the present embodiment, the reference shape is a single elliptical shape with an oblateness smaller than a threshold, and when determining that the shape of the corneal reflex image 113 is not included in the reference shape, the light source control unit 22 changes the light source for emitting the detection light. With this configuration, the light source for emitting the detection light is changed when it is determined that the shape of the corneal reflex image 113 is not included in a single elliptical range with the oblateness smaller than the threshold, so that it is possible to arrange the corneal reflex image 113 of the detection light in the cornea of the subject.

In the line-of-sight detection device 100 according to the present embodiment, the plurality of light sources include the first light source 103A and the second light source 103B that are arranged below the display unit 101 and the third light source 103C and the fourth light source 103D that are arranged above the display unit 101, and the light source control unit 22 changes the light source for emitting the detection light between the lower light source and the upper light source. With this configuration, it is possible to infallibly arrange the reflected image of the detection light in the cornea of the subject.

The embodiments of the present disclosure have been described above; however, the above embodiments are not limited by the details of the embodiments. The components described above include one that can be easily thought of by a person skilled in the art, one that is practically identical, and one that is within an equivalent range. Further, the components described above may be combined appropriately. Furthermore, within the scope not departing from the gist of the embodiments as described above, various omission, replacement, and modifications of the components may be made.

For example, in the embodiment as described above, the example has been described in which the plurality of light sources include the lower light source (the first light source 103A and the second light source 103B) that is arranged below the display unit 101 and the upper light source (the third light source 103C and the fourth light source 103D) that is arranged above the display unit 101, but embodiments are not limited to this example. For example, it may be possible to arrange light sources at a left side portion and a right side portion of the display unit 101 in addition to the lower light source and the upper light source or instead of at least one of the lower light source and the upper light source.

Furthermore, in the embodiment as described above, the example has been described in which the two light sources (the third light source 103C and the fourth light source 103D) are arranged as the upper light source, but embodiments are not limited to this example. For example, it may be possible to arrange a single light source as the upper light source.

Moreover, in the embodiment as described above, the example has been described in which the first camera 102A and the second camera 102B are arranged below the display unit 101, but embodiments are not limited to this example. The first camera 102A and the second camera 102B may be arranged in the upper part or a side part of the display unit 101.

Furthermore, in the embodiment as described above, the example has been described in which the light source control unit 22 causes one of the lower light source (the first light source 103A and the second light source 103B) and the upper light source (the third light source 103C and the fourth light source 103D) to emit detection light. In addition, the light source control unit 22 may sequentially cause both of the lower light source and the upper light source to emit the detection light and calculate a distance between the pupil center and the corneal reflex center in the image data of the eyeball 111. In this case, the gaze point detection unit 26 may detect a gaze point by using the image data that is obtained when the detection light is emitted by the one of the lower light source and the upper light source by which the calculated distance is shorter as compared to the other one of the lower light source and the upper light source. Moreover, the light source control unit 22 may sequentially cause both of the lower light source and the upper light source to emit the detection light and calculate each of the corneal reflex images in the image data of the eyeball 111. In this case, the gaze point detection unit 26 may detect the gaze point by using the image data that is obtained when the detection light is emitted from one of the lower light source and the upper light source by which the shape of the corneal reflex image is closer to the reference shape as compared to the other one of the lower light source and the upper light source.

The present disclosure includes a matter that contributes to realization of "Good Health and Well-Being" of SDGs and contributes to value creation by healthcare products and services.

The line-of-sight detection program described above may be provided by being stored in a non-transitory computer-readable storage medium, or may be provided via a network such as the Internet. Examples of the computer-readable storage medium include optical discs such as a digital versatile disc (DVD) and a compact disc (CD), and other types of storage devices such as a hard disk and a semiconductor memory.

According to the present disclosure, it is possible to provide a line-of-sight detection device, a line-of-sight detection method, and a line-of-sight detection program capable of preventing reduction in detection accuracy.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A line-of-sight detection device comprising:
a display unit that displays an image;
a plurality of light sources configured to emit detection light to apply the detection light to at least one of eyeballs of a subject;
an imaging unit configured to capture an image of the eyeball to which the detection light is applied;
a position detection unit configured to detect, from the captured image, a position of a pupil center that indicates a center of a pupil of the eyeball to which the detection light is applied and a position of a corneal reflex center that indicates a center of a corneal reflex;
a gaze point detection unit configured to calculate a position of a gaze point of the subject based on the position of the pupil center and the position of the corneal reflex center; and
a light source control unit configured to change the light source for emitting the detection light among the plurality of light sources based on a target distance between the pupil center and the corneal reflex center.

2. The line-of-sight detection device according to claim 1, wherein the light source control unit is configured to, if the target distance between the pupil center and the corneal reflex center is equal to or larger than a predetermined threshold when a light source of the plurality of light sources emits the detection light, change the light source for emitting the detection light to another light source.

3. The line-of-sight detection device according to claim 2, wherein the predetermined threshold is a distance at which a reflected image of the detection light is formed at a position so as not to protrude from a cornea of the subject, the distance being calculated in advance in a calibration process.

4. The line-of-sight detection device according to claim 1, wherein
the plurality of light sources include a lower light source that is arranged below the display unit and an upper light source that is arranged above the display unit,
the target distance is a distance in a vertical direction, and
the light source control unit is configured to change the light source for emitting the detection light between the lower light source and the upper light source.

5. The line-of-sight detection device according to claim 1, wherein the light source control unit is configured to change the light source for emitting the detection light based on whether a shape of a reflected image of the detection light in the image of the eyeball is included in a reference shape.

6. A line-of-sight detection method comprising:
displaying an image on a display unit;
emitting detection light from a plurality of light sources to apply the detection light to at least one of eyeballs of a subject;
capturing an image of the eyeball to which the detection light is applied;
detecting, from the captured image, a position of a pupil center that indicates a center of a pupil of the eyeball to which the detection light is applied and a position of a corneal reflex center that indicates a center of a corneal reflex;
calculating a position of a gaze point of the subject based on the position of the pupil center and the position of the corneal reflex center; and
changing the light source for emitting the detection light among the plurality of light sources based on a target distance between the pupil center and the corneal reflex center.

7. A non-transitory computer-readable storage medium storing a program for detecting a line-of-sight, the program causing a computer to execute:
displaying an image on a display unit;
emitting detection light from a plurality of light sources to apply the detection light to at least one of eyeballs of a subject;
capturing an image of the eyeball to which the detection light is applied;
detecting, from the captured image, a position of a pupil center that indicates a center of a pupil of the eyeball to which the detection light is applied and a position of a corneal reflex center that indicates a center of a corneal reflex;
calculating a position of a gaze point of the subject based on the position of the pupil center and the position of the corneal reflex center; and
changing the light source for emitting the detection light among the plurality of light sources based on a target distance between the pupil center and the corneal reflex center.

* * * * *